United States Patent
Villafranca

(10) Patent No.: US 12,357,596 B2
(45) Date of Patent: Jul. 15, 2025

(54) COMPOUNDS FOR PREVENTION AND TREATMENT OF OBESITY AND RELATED DISORDERS

(71) Applicant: ABREXA PHARMACEUTICALS, INC., San Diego, CA (US)

(72) Inventor: Jesus E. Villafranca, San Diego, CA (US)

(73) Assignee: ABREXA PHARMACEUTICALS, INC., San Diego, CA (US)

( * ) Notice: Subject to any disclaimer, the term of this patent is extended or adjusted under 35 U.S.C. 154(b) by 908 days.

(21) Appl. No.: 17/435,678

(22) PCT Filed: Mar. 2, 2020

(86) PCT No.: PCT/US2020/020707
§ 371 (c)(1),
(2) Date: Sep. 1, 2021

(87) PCT Pub. No.: WO2020/180821
PCT Pub. Date: Sep. 10, 2020

(65) Prior Publication Data
US 2022/0133657 A1 May 5, 2022

Related U.S. Application Data

(60) Provisional application No. 62/812,314, filed on Mar. 1, 2019.

(51) Int. Cl.
| | | |
|---|---|---|
| A61K 31/167 | (2006.01) | |
| A61K 31/15 | (2006.01) | |
| A61K 31/16 | (2006.01) | |
| A61P 3/04 | (2006.01) | |

(52) U.S. Cl.
CPC ............ *A61K 31/167* (2013.01); *A61P 3/04* (2018.01)

(58) Field of Classification Search
CPC ...... A61K 31/167; A61K 31/15; A61K 31/16; A61P 3/04
See application file for complete search history.

(56) References Cited

U.S. PATENT DOCUMENTS

| | | |
|---|---|---|
| 4,017,540 A | 4/1977 | Kaugars et al. |
| 2007/0238700 A1 | 10/2007 | Wizenberg et al. |
| 2010/0004302 A1 | 1/2010 | Erickson-Miller et al. |
| 2010/0305181 A1 | 12/2010 | Schubert |
| 2017/0174614 A1 | 6/2017 | Farr et al. |

OTHER PUBLICATIONS

ObesityPrevention, 2024, https://www.hopkinsmedicine.org/health/conditions-and-diseases/obesity/preventing-obesity#:~:text=Improving%20eating%20habits%20and%20increasing,of%20fruits%20and%20vegetables%20daily.*
European Patent Office, European Supplementary Search Report issued in EP Patent Application No. 20767302.1, Oct. 28, 2022, pp. 1-7.
Payahoo et al., "Oleoylethanolamide increases the expression of PPAR-A and reduces appetite and body weight in obese people: A clinical trial", Appetite, Sep. 1, 2018, pp. 44-49, vol. 128.
Blundell et al., "Effects of once-weekly semaglutide on appetite, energy intake, control of eating, food preference and body weight in subjects with obesity", Diabetes Obesity and Metabolism, May 5, 2017, pp. 1242-1251, vol. 19(9).
China National Intellectual Property Administration, English Translation of Office Action issued in CN 202080030234.4, Jun. 20, 2024, pp. 1-5.
Prior et al., "Selecting for neurogenic potential as an alternative for Alzheimer's disease drug discovery", Alzheimer's & Dementia, 2016, pp. 678-686, vol. 12.
Patent Cooperation Treaty, International Search Report issued in PCT/US2020/020707, Apr. 30, 2020, pp. 1-4.
Wilding et al., "The importance of weight management in type 2 diabetes mellitus", International Journal of clinical Practice, Jun. 2014, pp. 682-691, vol. 68(6).
Pubchem CID 9679644, "N-Phenyl-N'-[(E)-phenylmenthylidene]acetohydrazide", Oct. 24, 2006, pp. 1-9, retrieved from the Internet <URL:https://pubchem.ncbi.nlm.nih.gov/compound/9679644>.

* cited by examiner

*Primary Examiner* — Sun Jae Yoo
(74) *Attorney, Agent, or Firm* — Pillsbury Winthrop Shaw Pittman LLP (CV)

(57) ABSTRACT

Presented herein, in certain aspects, are methods of treating or preventing obesity, assisting or inducing weight loss, suppressing apatite, or inhibiting weight gain in a subject by administering a compound of the invention to a subject.

18 Claims, 8 Drawing Sheets

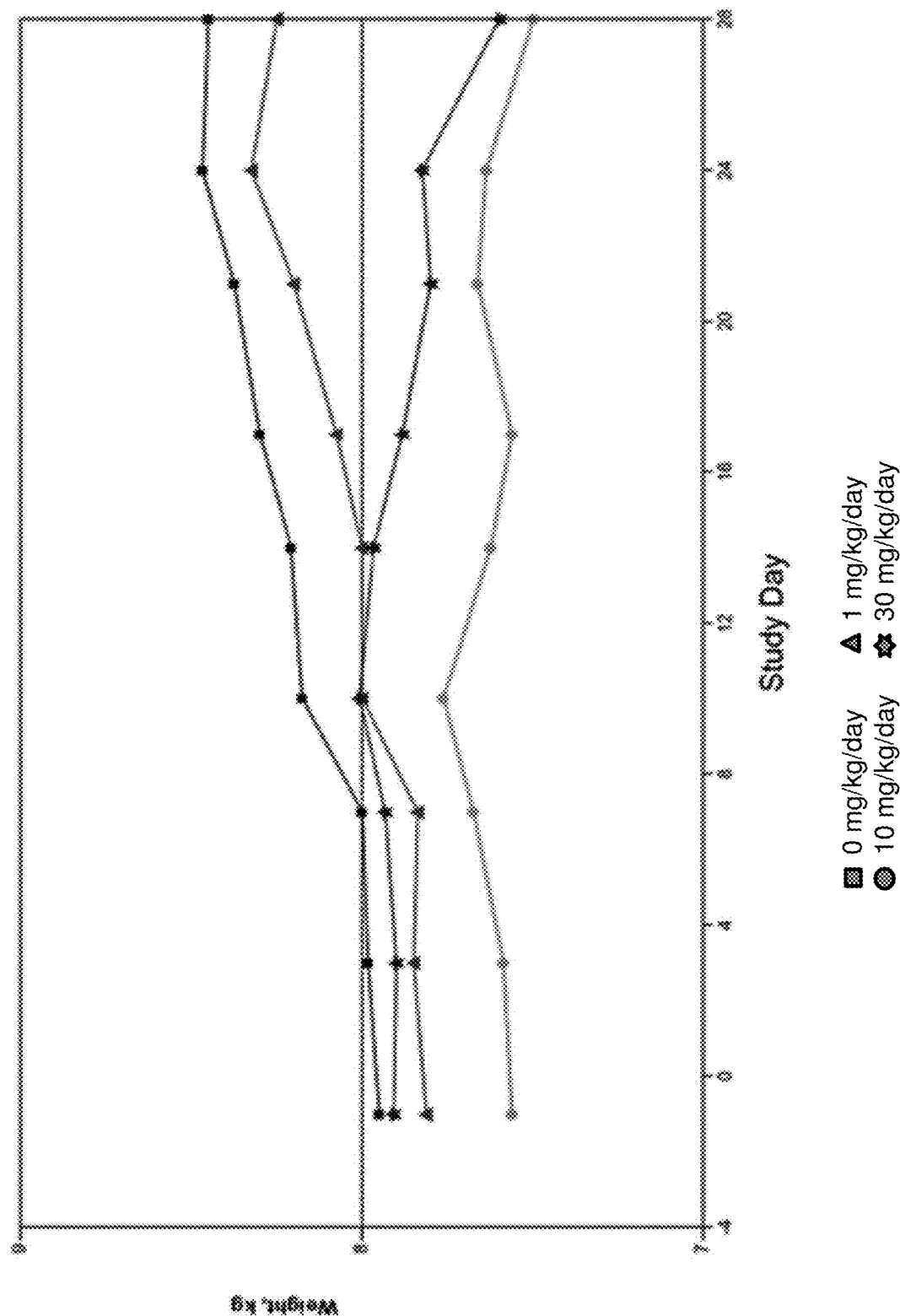

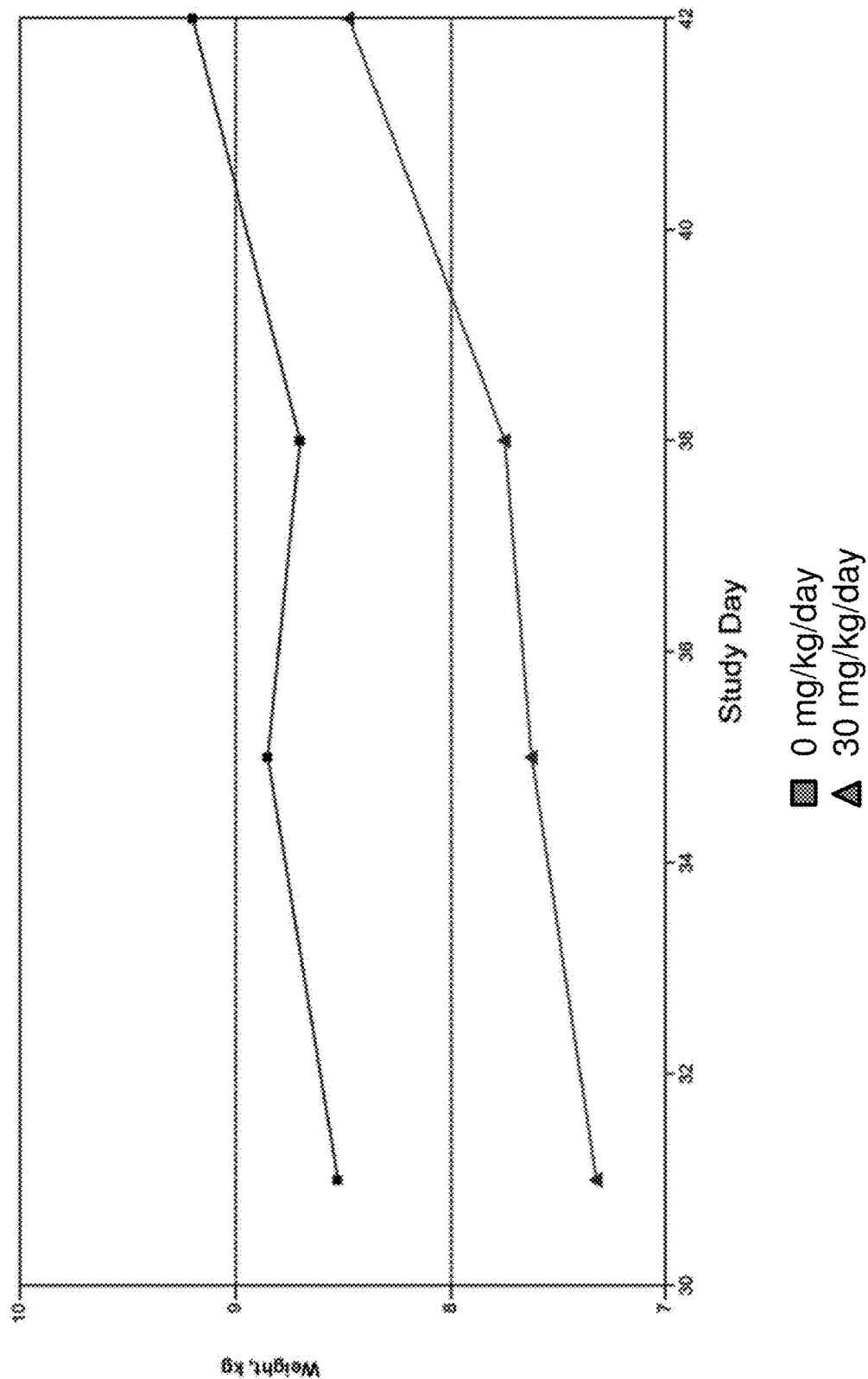

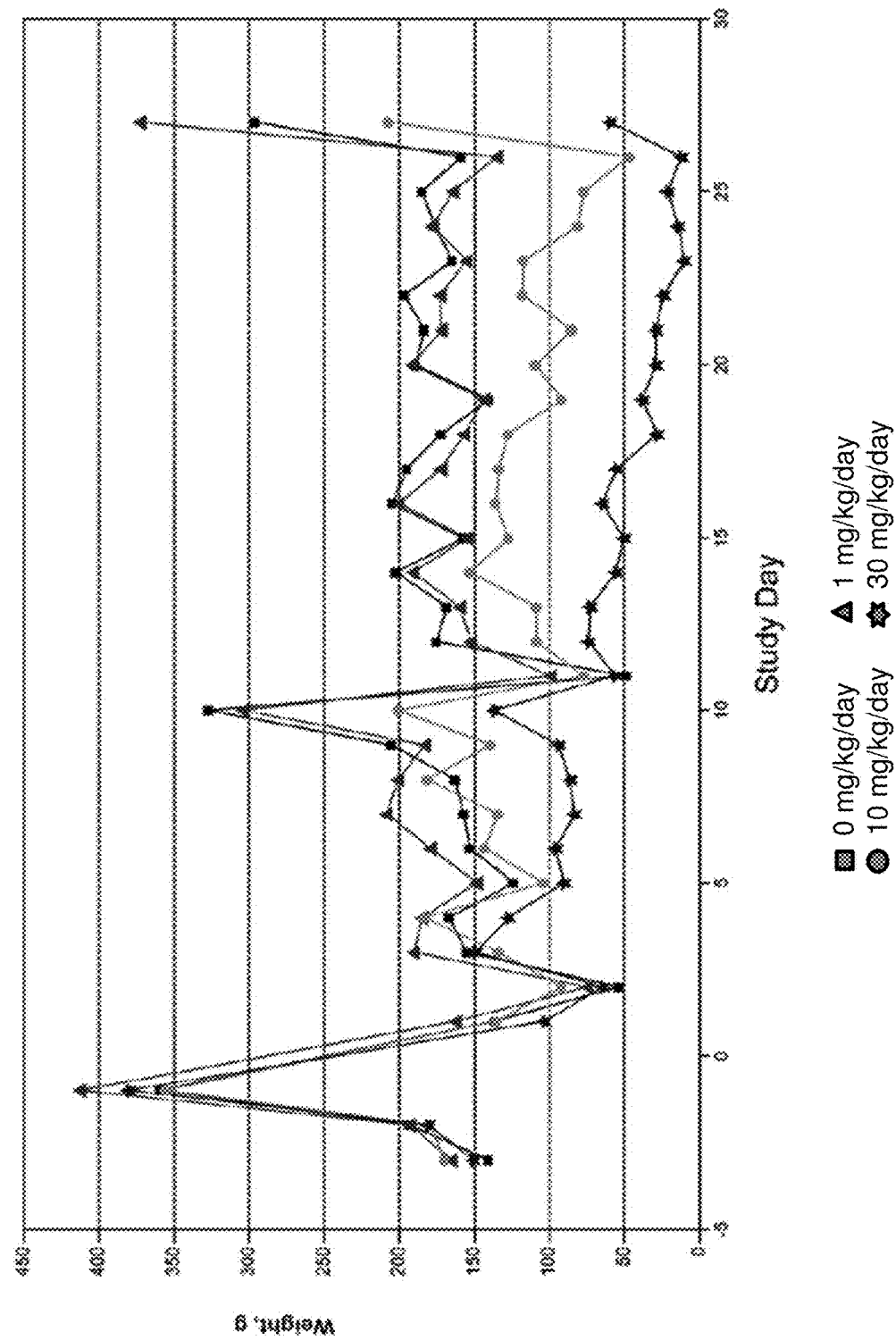

COMPOUNDS FOR PREVENTION AND TREATMENT OF OBESITY AND RELATED DISORDERS

FIELD OF THE INVENTION

The present invention relates to uses of compounds for the treatment and/or prevention of obesity, inducing weight loss and/or suppressing apatite.

BACKGROUND

Obesity is a common clinical disorder in both highly developed and newly emerging countries. Over 300 million adults are deemed to be clinically obese worldwide. There is also substantial clinical and epidemiological evidence accumulated to date that reveals that obesity is correlated with cardiovascular disease, hypertension, and diabetes.

The National Institutes of Health offers a suggested definition of obesity as a body mass index (or "BMI") of 30 and above. BMI correlates strongly in adults with the total body fat content. BMI can be mathematically calculated by dividing a subject's weight (in kilograms) by a subject's height (in meters squared). A BMI of 30 typically suggests that a subject is 30 pounds overweight.

Despite all of the existing research, there appears to be a very limited number of ways to generate a meaningful weight loss for an obese human.

SUMMARY

Presented herein, in certain aspects, is a method of treating or preventing obesity, assisting or inducing weight loss, suppressing apatite, and/or inhibiting weight gain in a subject which method comprises administering a therapeutically effective amount of a compound disclosed herein (e.g., sometimes referred to herein as a compound of the invention) to a subject. In some embodiments, a compound of the invention comprises a structure of any one of Formulas I to IV disclosed herein, or a pharmaceutically acceptable salt, stereoisomer or tautomer thereof. In certain embodiments, a compound of the invention is included in a pharmaceutical composition. In some embodiments, a compound of the invention comprises the structure of Formula IV;

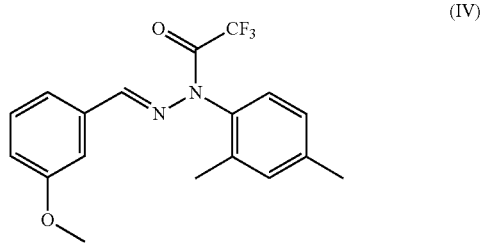 [SMILES: COc1cccc(/C=N/N(C(=O)C(F)(F)F)c2ccc(C)cc2C)c1]

(IV)

or a pharmaceutically acceptable salt, stereoisomer or tautomer thereof.

In some embodiments a subject is human. In some embodiments a compound of the invention is administered at a dose of 0.1 mg/kg to 100 mg/kg. In some embodiments a compound of the invention is administered at a dose of 5 mg/kg to 100 mg/kg. In some embodiments a compound of the invention is administered once per day, or twice per day. In certain embodiments, a compound of the invention is administered orally or intravenously.

BRIEF DESCRIPTION OF THE DRAWINGS

The drawings illustrate embodiments of the technology and are not limiting.

FIGS. 1A and 1B show a graphical representation of the mean body weight (y-axis) over time (x-axis; Study Days) of beagle dogs treated with J147 at 1 mg/kg/day (triangles), 10 mg/kg/day (circles), 30 mg/kg/day (stars) or with control (i.e., 0 mg/kg/day of J147; squares). FIG. 1A shows mean body weight values for males dogs. FIG. 1B shows mean body weight values for females dogs.

FIGS. 1C and 1D show a graphical representation of the mean body weight (Y-axis) over time (x-axis; Study Days) of beagle dogs during the recovery period (i.e. after administration of a final treatment) of dogs previously treated with J147 at 30 mg/kg/day (triangles) or with control (i.e., 0 mg/kg/day of J147; squares). FIG. 1C shows mean body weight values for males dogs. FIG. 1D shows mean body weight values for females dogs.

FIGS. 2A and 2B show a graphical representation of food consumption (y-axis; grams/day) over time (x-axis; Study Days) of beagle dogs treated with J147 at 1 mg/kg/day (triangles), 10 mg/kg/day (circles), 30 mg/kg/day (stars) or with control (i.e., 0 mg/kg/day of J147; squares). FIG. 2A shows mean food consumption for males dogs. FIG. 2B shows mean food consumption for females dogs.

FIG. 2C shows mean food consumption for males dogs. FIG. 2D shows mean food consumption for females dogs.

DETAILED DESCRIPTION OF THE INVENTION

Figure 1B:
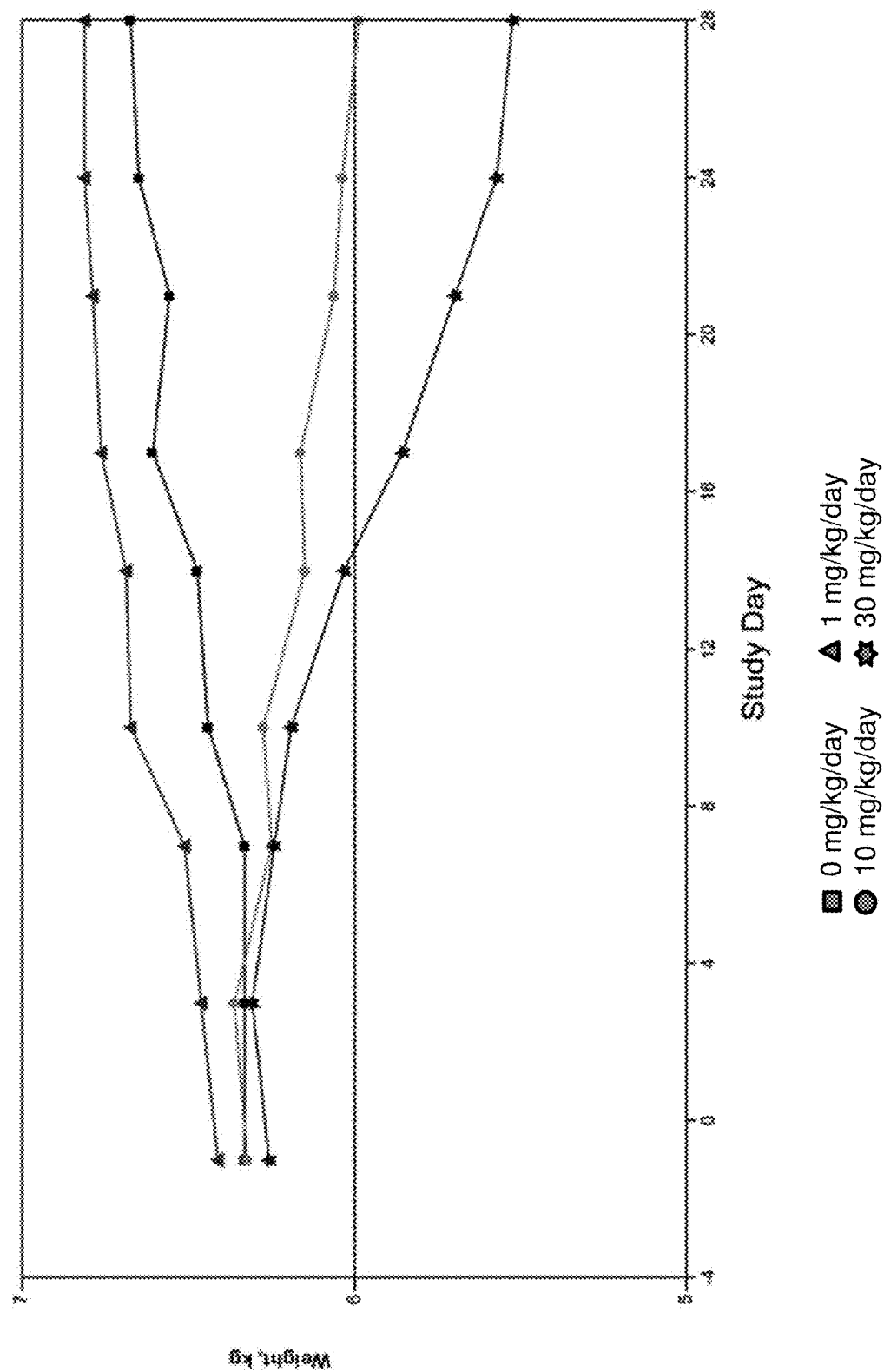

Presented herein are compounds for treatment and/or prevention of obesity, inducing weight loss, preventing weight gain and/or suppressing apatite.

Compounds

In some embodiments, a compound of the invention comprises the structure of Formula I;

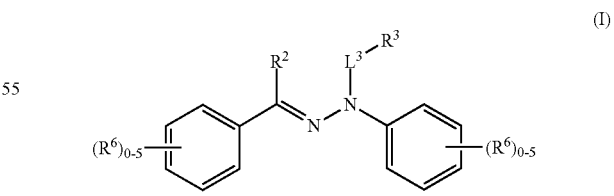

(I)

or a pharmaceutically acceptable salt, stereoisomer or tautomer thereof. In some embodiments of Formula I, $R^2$ is hydrogen (H) or methyl; $R^3$ is a methyl, a fluorine substituted alkyl (e.g., fluoromethyl, difluoromethyl, or trifluoromethyl), or a bromine substituted alkyl (e.g., bromomethyl, dibromomethyl, tribromomethyl); $L^3$ is a carbonyl; and $R^6$ at each occurrence is independently selected from alkyl, substituted alkyl, alkenyl, substituted alkenyl, cycloalkyl, substituted cycloalkyl, hydroxyl, methoxy, alkoxy, substituted alkoxy, aryloxy, substituted aryloxy, mercapto, alkylthio, arylthio, carbonyl, carboxyl, aryl, substituted aryl, substituted heterocyclic, halogen, cyano, cyanoalkyl, amine, methyl amine, dimethyl amine, nitro, amino, amidino, carbamate, $CF_3$, $OCF_3$, $S(O)_nR^7$, and $C(O)R^8$, or two $R^6$ at adjacent positions combine to form an optionally substituted heteroaryl or heteroalkyl ring fused with the adjoining phenyl moiety; where $R^7$ is selected from H, $R^9$, $NH_2$, $HNR^9$ and $NR^9R^{10}$; $R^8$ is selected from OH, $OR^9$, $NH_2$, $NHR^9$ and $NR^9R^{10}$; where $R^9$ and $R^{10}$ at each occurrence are independently an optionally substituted alkyl; and n is 1 or 2.

In certain embodiments of Formula I, $R^6$ at each occurrence is independently selected from alkyl, substituted alkyl, alkenyl, substituted alkenyl, hydroxyl, alkoxy, methoxy, substituted alkoxy, halogen, carbonyl, carboxyl, or $C(O)R^8$; and in certain such aspects, $R^6$ at each occurrence is methyl, methoxy, perfluoromethyl, perfluoromethoxy, hydroxyl, Cl, F, or I. In some embodiments of Formula I, $L^3$ is carbonyl, $R^3$ is $CF^3$, $R^2$ is H, and $R^6$ is null or H at every occurrence. In some embodiments of Formula I, $L^3$ is carbonyl, $R^3$ is $CF_3$, $R^2$ is H, and $R^6$ is independently selected from methyl or methoxy, at each occurrence. In some embodiments of Formula I, $L^3$ is carbonyl, $R^3$ is $CF_3$, $R^2$ is methyl, and $R^6$ is independently selected from methyl or methoxy, at each occurrence.

In some embodiments, a compound of the invention comprises the structure of Formula II;

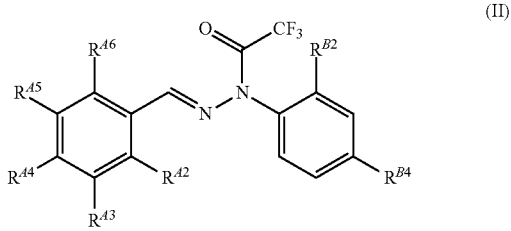

or a pharmaceutically acceptable salt, stereoisomer or tautomer thereof, where:
(i) $R^{A2}$, $R^{A4}$, $R^{A5}$, and $R^{A6}$ is H, $R^{A3}$ is methoxy, $R^{B2}$ is methyl, and $R^{B4}$ is methyl;
(ii) $R^{A2}$, $R^{A3}$, $R^{A5}$, and $R^{A6}$ is H, $R^{A4}$ is methoxy, $R^{B2}$ is methyl, and $R^{B4}$ is methyl;
(iii) $R^{A2}$, $R^{A3}$, $R^{A4}$, $R^{A5}$, and $R^{A6}$ is H, $R^{B2}$ is H, and $R^{B4}$ is H;
(iv) $R^{A2}$, $R^{A3}$, $R^{A4}$, $R^{A5}$, and $R^{A6}$ is H, $R^{B2}$ is methyl, and $R^{B4}$ is methyl;
(v) $R^{A2}$, $R^{A4}$, $R^{A5}$, and $R^{A6}$ is H, $R^{A3}$ is methoxy, $R^{B2}$ is H, and $R^{B4}$ is H;
(vi) $R^{A2}$, $R^{A3}$, $R^{A4}$, $R^{A5}$, and $R^{A6}$ is H, $R^{B2}$ is H, and $R^{B4}$ is methyl;
(vii) $R^{A2}$, $A^{A4}$, $R^{A5}$, and $R^{A6}$ is H, $R^{A3}$ is methoxy, $R^{B2}$ is H, and $R^{B4}$ is methyl;
(viii) $R^{A2}$, $R^{A3}$, $R^{A4}$, $R^{A5}$, and $R^{A6}$ is H, $R^{B2}$ is methyl, and $R^{B4}$ is H;
(ix) $R^{A2}$, $R^{A4}$, $R^{A5}$, and $R^{A6}$ is H, $R^{A3}$ is methoxy, $R^{B2}$ is methyl, and $R^{B4}$ is H;
(x) $R^{A2}$, $R^{A3}$, $R^{A5}$, and $R^{A6}$ is H, $R^{A4}$ is COOH, $R^{B2}$ is methyl, and $R^{B4}$ is methyl;
(xi) $R^{A2}$, $R^{A4}$, and $R^{A5}$ is H, $R^{A3}$ and $R^{A6}$ is hydroxyl, $R^{B2}$ is methyl, and $R^{B4}$ is methyl;
(xii) $R^{A2}$, $R^{A4}$, and $R^{A6}$ is H, $R^{A3}$ and $R^{A5}$ is hydroxyl, $R^{B2}$ is methyl, and $R^{B4}$ is methyl;
(xiii) $R^{A2}$, $R^{A4}$, and $R^{A5}$ is H, $R^{A3}$ is methoxy, $R^{A6}$ is F, $R^{B2}$ is H, and $R^{B4}$ is Cl;
(xiv) $R^{A3}$ and $R^{A5}$ is H, $R^{A2}$ and $R^{A6}$ is F, $R^{A4}$ is hydroxyl, $R^{A6}$ is F, $R^{B2}$ is H, and $R^{B4}$ is F;
(xv) $R^{A2}$, $R^{A4}$, and $R^{A6}$ is H, $R^{A3}$ is hydroxyl, $R^{A5}$ is F, $R^{B2}$ is H, and $R^{B4}$ is F; or
(xvi) $R^{A2}$, $R^{A5}$, and $R^{A6}$ is H, $R^{A3}$ and $R^{A4}$ taken together are —O—$CH_2$—O—, $R^{A5}$ is F, $R^{B2}$ is H, and $R^{B4}$ is F.

In some embodiments of the compound of Formula II, $R^{A2}$, $R^{A5}$, and $R^{A6}$ are H, $R^{A3}$ is methoxy, $R^{B2}$ and $R^{B4}$ are methyl, and $R^{A4}$ is selected from H, $NO_2$, OH, methoxy, phenol, methyl, Fluorine (F), $N(CH_3)_2$, $CHC(CN)_2$ and O-tert-butyldimethylsilyl (OTBDMS). In some embodiments of the compound of Formula II, $R^{A2}$, $R^{A4}$, $R^{A5}$, and $R^{A6}$ are H, $R^{A3}$ is methoxy, $R^{B2}$ is methyl, and $R^{B4}$ is methyl. In some embodiments of the compound of Formula II, $R^{A2}$, $R^{A3}$, $R^{A5}$, and $R^{A6}$ are H, $R^{A4}$ is methoxy, $R^{B2}$ is methyl, and $R^{B4}$ is methyl. In some embodiments of the compound of Formula II, $R^{A2}$, $R^{A3}$, $R^{A4}$, $R^{A5}$, and $R^{A6}$ are H, $R^{B2}$ is methyl, and $R^{B4}$ is methyl. In some embodiments of the compound of Formula II, $R^{A2}$, $R^{A4}$, $R^{A5}$, and $R^{A6}$ are H, $R^{A3}$ is methoxy, $R^{B2}$ is H, and $R^{B4}$ is H. In some embodiments of the compound of Formula II, $R^{A2}$, $R^{A3}$, $R^{A4}$, $R^{A5}$ and $R^{A6}$ are H, $R^{B2}$ is H, and $R^{B4}$ is methyl. In some embodiments of the compound of Formula II, $R^{A2}$, $R^{A3}$, $R^{A4}$, $R^{A5}$ and $R^{A6}$ are H, $R^{B2}$ is H, and $R^{B4}$ is methyl. In some embodiments of the compound of Formula II, $R^{A2}$, $R^{A4}$, $R^{A5}$ and $R^{A6}$ are H, $R^{A3}$ is methoxy, $R^{B2}$ is H, and $R^{B4}$ is methyl. In some embodiments of the compound of Formula II, $R^{A2}$, $R^{A4}$, $R^{A5}$ and $R^{A6}$ are H, $R^{A3}$ is methoxy, $R^{B2}$ is methyl, and $R^{B4}$ is H. In some embodiments of the compound of Formula II, $R^{A2}$, $R^{A3}$, $R^{A4}$, $R^{A5}$ and $R^{A6}$ are H, $R^{B2}$ is methyl, and $R^{B4}$ is H. In some embodiments of the compound of Formula II, $R^{A2}$, $R^{A3}$, $R^{A5}$ and $R^{A6}$ are H, $R^{A4}$ is a carboxyl, $R^{B2}$ is methyl, and $R^{B4}$ is methyl. In some embodiments of the compound of Formula II, $R^{A2}$, $R^{A4}$, $R^{A5}$ and $R^{A6}$ are H, $R^{A3}$ is a carboxyl, $R^{B2}$ is methyl, and $R^{B4}$ is methyl.

In some embodiments, a compound of the invention comprises the structure of Formula III;

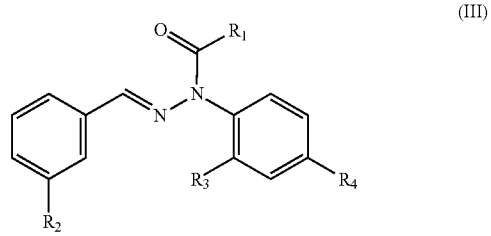

or a pharmaceutically acceptable salt, stereoisomer or tautomer thereof, where $R_1$ is methyl, fluoromethyl, difluoromethyl, trifluoromethyl, bromomethyl, dibromomethyl or tribromomethyl; $R_2$ is methyl, methoxy, hydroxyl, halogen, $CF_3$, $OCH_3$, $OCF_3$ or $OCBr_3$; and $R_3$ and $R_4$ are independently selected from hydrogen, hydroxyl, a halogen (e.g., Cl, F or Br), methyl, a methoxy, and an amine. In some embodiments of Formula III, $R_1$ is $CF_3$ (trifluoromethyl), $R_2$ is $OCH_3$, and $R_3$ and $R_4$ are methyl. In some embodiments of Formula III, $R_1$ is $CF_3$ (trifluoromethyl), $R_2$ is $OCF_3$, and $R_3$ and $R_4$ are methyl In some embodiments, a compound of the invention comprises the structure of Formula IV below, or a pharmaceutically acceptable salt, stereoisomer or tautomer thereof.

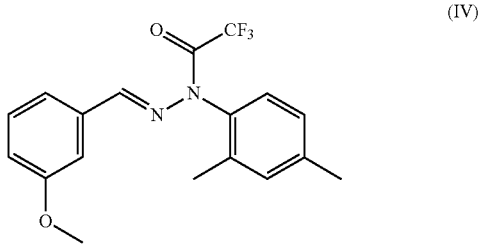 [SMILES: COc1cccc(/C=N/N(C(=O)C(F)(F)F)c2ccc(C)cc2C)c1]

(IV)

The structure of Formula IV is sometimes referred to herein as "J147".

The following terms have the respective definitions set out below.

"Alkyl" refers to straight or branched chain alkyl radicals having in the range of about 1 up to about 12 carbon atoms (e.g., methyl, ethyl, propyl, butyl, and the like). "Substituted alkyl" refers to alkyl further bearing one or more substituents (e.g., 1, 2, 3, 4, or even 5) as set forth herein. "Optionally substituted alkyl" refers to alkyl or substituted alkyl.

"Cycloalkyl" refers to cyclic ring-containing groups containing in the range of about 3 up to about 12 carbon atoms. "Substituted cycloalkyl" refers to cycloalkyl further bearing one or more substituents (e.g., 1, 2, 3, 4, or even 5) selected from alkyl, substituted alkyl, as well as any of the substituents set forth herein. "Optionally substituted cycloalkyl" refers to cycloalkyl or substituted cycloalkyl.

"Heterocycle," "heterocyclic" and like terms refer to cyclic (i.e., ring-containing) groups containing one or more heteroatoms (e.g., N, O, S, or the like) as part of the ring, and having in the range of 1 up to about 14 carbon atoms. "Substituted heterocyclic" and like terms refer to heterocycle further bearing one or more substituents (e.g., 1, 2, 3, 4, or even 5) as set forth herein. Exemplary heterocyclic moieties include saturated rings, unsaturated rings, and aromatic heteroatom-containing ring systems, e.g., epoxy, tetrahydrofuran, oxazoline, pyrrole, pyridine, furan, and the like. "Optionally substituted heterocycle" and like terms refer to heterocycle or substituted heterocycle.

Reference to "optionally substituted bicyclic ring" refers to a bicyclic ring structure as known in the art, optionally including substitutions as defined herein.

"Alkenyl" refers to straight, branched chain, or cyclic hydrocarbyl groups including from 2 to about 20 carbon atoms having at least one, 1-3, 1-2, or one, carbon to carbon double bond. "Substituted alkenyl" refers to alkenyl substituted at 1 or more, e.g., 1, 2, 3, 4, or even 5 positions, with substitution as described herein. "Optionally substituted alkenyl" refers to alkenyl or substituted alkenyl. In some embodiments, an alkenyl is ethylenyl or propylenyl. In certain embodiments, a substituted alkenyl is a substituted ethylenyl or substituted propylenyl. In some embodiments, ethylenyl or propylenyl is substituted with one or more CN moieties. For example, in some embodiments, a substituted ethylenyl comprises $(CN)_2C=CH—$.

"Aryl" refers to aromatic groups having in the range of 6 up to about 14 carbon atoms. "Substituted aryl" refers to aryl radicals further bearing one or more substituents (e.g., 1, 2, 3, 4, or even 5) selected from alkyl, substituted alkyl, cycloalkyl, substituted cycloalkyl, hydroxyl, alkoxy, aryloxy, mercapto, alkylthio, arylthio, carbonyl, aryl, substituted aryl, heterocyclic, substituted heterocyclic, halogen, trifluoromethyl, pentafluoroethyl, cyano, cyanoalkyl, nitro, amino, amido, amidino, carboxyl, carbamate, $SO_2X$, wherein X is H, R, $NH_2$, NHR or $NR_2$, $SO_3Y$, wherein Y is H, $NH_2$, NHR or $NR_2$, or C(O)Z, wherein Z is OH, OR, $NH_2$, NHR or $NR_2$, and the like. "Optionally substituted aryl" refers to aryl or substituted aryl.

"Aralkyl" refers to an alkyl group substituted by an aryl group. "Substituted aralkyl" refers to aralkyl further bearing one or more substituents (e.g., 1, 2, 3, 4, or even 5) selected from alkyl, substituted alkyl, cycloalkyl, substituted cycloalkyl, as well as any of the substituents set forth herein. Thus, aralkyl groups include benzyl, diphenylmethyl, and 1-phenylethyl ($—CH(C_6H_5)(CH_3)$) among others. "Optionally substituted aralkyl" refers to aralkyl or substituted aralkyl.

"Heteroaryl" refers to aromatic groups containing one or more heteroatoms (e.g., N, O, S, or the like) as part of the aromatic ring, typically having in the range of 2 up to about 14 carbon atoms, and "substituted heteroaryl" refers to heteroaryl radicals further bearing one or more substituents (e.g., 1, 2, 3, 4, or even 5) selected from alkyl, substituted alkyl, cycloalkyl, substituted cycloalkyl, as well as any of the substituents set forth above.

"Heteroaralkyl" and "heteroarylalkyl" refer to an alkyl group substituted by one or more heteroaryl groups. "Substituted heteroaralkyl" refers to heteroaralkyl further bearing one or more substituents (e.g., 1, 2, 3, 4, or even 5) selected from alkyl, substituted alkyl, cycloalkyl, substituted cycloalkyl, as well as any of the substituents set forth herein. "Optionally substituted heteroaralkyl" refers to heteroaralkyl or substituted heteroaralkyl.

"Halogen" and "halo" refer to fluorine, chlorine, bromine or iodine.

"Hydroxyl" and "hydroxy" refer to the functionality —OH.

"Alkoxy" denotes the group —OR, where R is alkyl. "Substituted alkoxy" denotes the group —OR, where R is substituted alkyl. "Optionally substituted alkoxy" refers to alkoxy or substituted alkoxy.

"Aryloxy" denotes the group —OR, where R is aryl. "Substituted aryloxy" denotes the group —OR, where R is substituted aryl. "Optionally substituted aryloxy" refers to aryloxy or substituted aryloxy.

"Mercapto" and "thiol" refer to the functionality —SH.

"Alkylthio" and "thioalkoxy" refer to the group —SR, $—S(O)_{n=1-2}—R$, where R is alkyl. "Substituted alkylthio" and "substituted thioalkoxy" refers to the group —SR, $—S(O)_{n=1-2}—R$, where R is substituted alkyl. "Optionally substituted alkylthio" and "optionally substituted thioalkoxy" refers to alkylthio or substituted alkylthio.

"Arylthio" denotes the group —SR, where R is aryl. "Substituted arylthio" denotes the group —SR, where R is substituted aryl. "Optionally substituted arylthio" refers to arylthio or substituted arylthio.

"Amino" refers to unsubstituted, monosubstituted and disubstituted amino groups, including the substituent —$NH_2$, "monoalkylamino," which refers to a substituent having structure —NHR, wherein R is alkyl or substituted alkyl, and "dialkylamino," which refers to a substituent of the structure —$NR_2$, wherein each R is independently alkyl or substituted alkyl.

"Amidino" denotes the group —$C(=NR^q)NR^rR^s$, wherein $R^q$, $R^r$, and $R^s$ are independently hydrogen or optionally substituted alkyl.

Reference to "amide group" embraces substituents of the structure —C(O)—$NR_2$, wherein each R is independently H, alkyl, substituted alkyl, aryl or substituted aryl as set forth above. When each R is H, the substituent is also referred to as "carbamoyl" (i.e., a substituent having the structure —C(O)—$NH_2$). When only one of the R groups is H, the substituent is also referred to as "monoalkylcarbamoyl" (i.e., a substituent having the structure —C(O)—NHR, wherein R is alkyl or substituted alkyl as set forth above) or "arylcarbamoyl" (i.e., a substituent having the structure —C(O)—NH(aryl), wherein aryl is as defined above, including substituted aryl). When neither of the R groups are H, the substituent is also referred to as "di-alkylcarbamoyl" (i.e., a substituent having the structure —C(O)—NR$_2$, wherein each R is independently alkyl or substituted alkyl as set forth above).

Reference to "carbamate" embraces substituents of the structure —O—C(O)—NR$_2$, wherein each R is independently H, alkyl, substituted alkyl, aryl or substituted aryl.

Reference to "ester group" embraces substituents of the structure —O—C(O)—OR, wherein each R is independently alkyl, substituted alkyl, aryl or substituted aryl.

"Acyl" refers to groups having the structure —C(O)R, where R is hydrogen, alkyl, aryl, and the like as defined herein. "Substituted acyl" refers to acyl wherein the substituent R is substituted as defined herein. "Optionally substituted acyl" refers to acyl and substituted acyl.

"Cyanoalkyl" refers to the group —R≡N, wherein R is an optionally substituted alkylenyl.

As used here, "substitution" denotes an atom or group of atoms that has been replaced with another atom or group of atoms (i.e., substituent), and includes all levels of substitution, e.g. mono-, di-, tri-, tetra-, penta-, or even hex-substitution, where such substitution is chemically permissible. Substitutions can occur at any chemically accessible position and on any atom, such as substitution(s) on carbon and any heteroatom, such as oxygen, nitrogen, or sulfur. For example, substituted moieties include those where one or more bonds to a hydrogen or carbon atom(s) contained therein are replaced by a bond to non-hydrogen and/or non-carbon atom(s). Substitutions can include, but are not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and heteroatoms in other groups as well known in the art.

Non-limiting examples of substituents include, without limitation, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR, —SR, —OC(O)R, —OC(S)R, —C(O)R, —C(S)R, —C(O)OR, —C(S)OR, —S(O)R, —S(O)$_2$R, —C(O)NHR, —C(S)NHR, —C(O)NRR, —C(S)NRR, —S(O)$_2$NHR, —S(O)$_2$NRR, —C(NR)NHR, —C(NH)NRR, —NHC(O)R, —NHC(S)R, —NRC(O)R, —NRC(S)R, —NHS(O)$_2$R, —NRS(O)$_2$R, —NHC(O)NHR, —NHC(S)NHR, —NRC(O)NH$_2$, —NRC(S)NH$_2$, —NRC(O)NHR, —NRC(S)NHR, —NHC(O)NRR, —NHC(S)NRR, —NRC(O)NRR, —NRC(S)NRR, —NHS(O)$_2$NHR, —NRS(O)$_2$NH$_2$, —NRS(O)$_2$NHR, —NHS(O)$_2$NRR, —NRS(O)$_2$NRR, —NHR, —NRR, where R at each occurrence is independently H, optionally substituted alkyl, optionally substituted aryl, or optionally substituted heteroaryl. Also contemplated is substitution with an optionally substituted hydrocarbyl moiety containing one or more of the following chemical functionalities: —O—, —S—, —NR—, —O—C(O)—, —O—C(O)—O—, —O—C(O)—NR—, —NR—C(O)—, —NR—C(O)—O—, —NR—C(O)—NR—, —S—C(O)—, —S—C(O)—O—, —S—C(O)—NR—, —S(O)—, —S(O)$_2$—, —O—S(O)$_2$—, —O—S(O)$_2$—O—, —O—S(O)$_2$—NR—, —O—S(O)—, —O—S(O)$_2$—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR—, —NR—C(S)—, —NR—C(S)—O—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NRP(O)R$_2$—, where R at each occurrence is independently H, optionally substituted alkyl, optionally substituted aryl, or optionally substituted heteroaryl.

In some embodiments, a compound of the invention includes isomers including stereoisomers (e.g., enantiomer and diasteromers), constitutional isomers, tautomers, conformational isomers, and geometric isomers of a compound disclosed herein.

Exemplary constitutional isomers include for example without limitation, isomers resulting from different connectivity of functionalities forming the compounds of the invention, for example, 1-propyl versus 2-propyl substitution, and the like. Constitutional isomers in combination with tautomerization additionally embrace bonding rearrangements involving the migration of double bonds and substituents. For example, tautomerization in combination with a 1-3 pleiotropic hydrogen shift can result in constitutional isomerism.

Exemplary conformational isomers include for example without limitation, isomers produced by rotation about a bond wherein the rotation is hindered to the extent that separable isomers result, as well known in the art.

Exemplary geometrical isomers include double bonds in e.g., the "E" or "Z" configuration, as well known in the art.

Compounds of the invention can be readily prepared using a suitable synthetic method. For example, curcumin can be condensed with phenyl hydrazine by warming to reflux overnight in toluene. Optionally, a catalytic amount of acid (HCl) can be employed. In some embodiments, pure curcumin (vs. technical grade) and freshly distilled phenyl hydrazine can be employed.

As another example, 3-methoxy benzaldehyde can be condensed with 2,4-dimethylphenyl hydrazine in methanol employing standard hydrazone preparation conditions (e.g., heating in the microwave to speed the reaction time). Next, the free NH is acylated with TFAA (trifluoroacetic anhydride) plus catalytic (0.1%) amounts of DMAP (dimethylamino pyridine), THE (tetrahydrofuran) or DCM (dichloromethane).

In some embodiments, $CF_3$ substituted triazoles can be prepared by 1,3-dipolar cycloaddition between suitable aryltrifluoromethylacetylenes and aryl azides. Regioselectivity can be obtained by utilizing a suitable click chemistry (e.g., see Huisgen R. (1984) 1,3-*Dipolar Cycloaddition Chemistry*, pp. 1-176, Lodon:Wiley; Padwa (1991) *Comprehensive Organic Synthesis*, Vol. 4:pp. 1069-1109, Oxford: Pergamon; and Fan & Katritzky (1996) *Comprehensive Heterocyclic Chemistry II*, Vol. 4: pp. 101-126, Oxford: Pergamon). Additional methods of generating compounds disclosed herein can be found in Lima et al., (2015) *Chem. Commun.* 51:10784-10796 and Kim et al., (2105) *Org. Biomol. Chem.* 13:9564-9569.

In some embodiments, a compound of the invention is provided in the form of pharmaceutically acceptable salt. A compound of the invention can be complexed with any suitable inorganic or organic salt. In some embodiments, a salt of a compound of the invention is prepared by reacting a compound of the invention with a suitable organic or inorganic acid or base. Non-limiting examples of organic salts contemplated for use herein with a compound of the invention include methanesulfonate, acetate, oxalate, adipate, alginate, aspartate, valerate, oleate, laurate, borate, benzoate, lactate, phosphate, toluenesulfonate (tosylate), citrate, malate, maleate, fumarate, succinate, tartrate, napsylate, methanesulfonate, 2-naphthalenesulfonate, nicotinate, benzenesulfonate, butyrate, camphorate, camphorsulfonate, cyclopentanepropionate, digluconate, dodecylsulfate, glucoheptanoate, glycerophosphate, heptanoate, hexanoate, undecanoate, 2-hydroxyethanesulfonate, ethane sulfonate, and the like. In some embodiments, inorganic salts can be formed from inorganic acids such as sulfate, bisulfate, hemisulfate, hydrochloride, chlorate, perchlorate, hydrobromide, hydroiodide, and the like. Non-limiting examples of a base salt include ammonium salts; alkali metal salts such as sodium salts, potassium salts, and the like; alkaline earth metal salts such as calcium salts, magnesium salts, and the like; salts with organic bases such as dicyclohexylamine salts, N-methyl-D-glucamine, phenylethylamine, and the like; and salts with amino acids such as arginine, lysine, and the like. Salt forms of a compound of the invention can be prepared employing a suitable method.

Methods and Indications

Presented herein are methods of treating and/or preventing obesity, assisting a subject in weight loss, inducing weight loss, suppressing apatite, and/or inhibiting weight gain in a subject comprising administering to the subject a therapeutically effective amount of a compound of the invention. In some embodiments, a method comprises assisting a subject in his/her efforts to lose weight wherein the subject is administered a compound disclosed herein. In some embodiments, a method comprises inducing weight loss in a subject wherein the subject is administered a compound disclosed herein. The term "weight" refers to a subject's body weight. The term "weight loss" refers to a reduction in a subject's body weight over time (e.g., as measured by days, weeks or months). In certain embodiments, a subject's body weight can be reduced by a method herein by 0.1% or more, 0.5% or more, 1% or more or 5% or more. In certain embodiments, a subject's body weight can be reduced by a method herein by 0.5 pounds or more, 1 pound or more, 5 pounds or more or 10 pounds or more. In certain embodiments, a subject's body weight can be reduced by a method herein by 1 to 150 pounds, 1 to 100 pounds or 1 to 50 pounds.

In some embodiments, a method comprises preventing obesity in a subject by administering a compound disclosed herein. Preventing obesity refers to a process of maintaining a subject's body weight at a healthy BMI (e.g., between about 18 and 29) and/or preventing a subject's BMI from exceeding a BMI of 29.9. In some embodiments, a method comprises treating obesity in a subject by administering a compound disclosed herein. Treating obesity refers to administering a compound of the invention to a subject having a BMI of 30 or greater with a goal of reducing the subject's BMI to a lower level. In some embodiments, treating obesity comprises reducing a subject's BMI by at least 0.1, at least 0.5, at least 1, or sometimes by at least 5. In some embodiments, treating obesity comprises inducing weight loss.

In some embodiments, a method comprises inhibiting, slowing or preventing weight gain in a subject by administering a compound of the invention to the subject. In some embodiments a method of inhibiting, slowing or preventing weight gain as disclosed herein can inhibit, slow or prevent an increase in a subject's body weight over time (e.g., over a period of days, weeks or years).

In some embodiments, a method comprises suppressing apatite in a subject by administering a compound of the invention to the subject.

Subjects

The term "subject" refers to a mammal. Any suitable mammal can be treated by a method or composition described herein. Non-limiting examples of mammals include a human, non-human primate (e.g., ape, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a subject is a non-human primate or a human. In some embodiments a subject is a human. A subject can be any age or at any stage of development (e.g., an adult, teen, child, infant, or a mammal in utero). A subject can be male or female.

In some embodiments, a subject is overweight. In some embodiments, a subject has a BMI of 30 or greater. In some embodiments a subject is obese. In some embodiments, a subject has an eating disorder. In certain embodiments a subject has or is suspected of having bulimia. In certain embodiments a subject has or is suspected of having a compulsive eating disorder or a binge eating disorder. In certain embodiments a subject has a history of compulsive overeating or binge eating. In certain embodiments a subject has a history of eating over 3000 calories/day. In certain embodiments a subject has a history of eating over 5000 calories/day. In certain embodiments, a subject is a human having a desire to lose weight.

In certain embodiments, a subject has or is suspected of having diabetes. In certain embodiments, a subject has or is suspected of having cardiovascular disease. In certain embodiments, a subject is at risk of having or at risk of developing diabetes, heart disease or cardiovascular disease.

Pharmaceutical Compositions

In some embodiments, a composition or pharmaceutical composition comprises a compound of the invention. In some embodiments, a composition or pharmaceutical composition comprises a therapeutically effective amount of a compound of the invention. In some embodiments, a composition or pharmaceutical composition comprises a compound disclosed herein in an amount in a range of 1 μg to 1000 mg, 1 μg to 100 mg, or 10 μg to 100 μg. In some embodiments provided herein is a pharmaceutical composition comprising a compound of the invention for use in treating and/or preventing obesity, assisting a subject in weight loss, inducing weight loss, suppressing apatite, and/or inhibiting weight gain in a subject. In some embodiments, a pharmaceutical composition comprises a compound of the invention and a pharmaceutically acceptable excipient, diluent, additive or carrier.

A pharmaceutical composition can be formulated for a suitable route of administration. In some embodiments a pharmaceutical composition is formulated for oral, subcutaneous (s.c.), intradermal, intramuscular, intraperitoneal and/or intravenous (i.v.) administration. In certain embodiments, a pharmaceutical composition contains formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogensulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In particular, a pharmaceutical composition can comprise any suitable carrier, formulation, or ingredient, the like or combinations thereof as listed in "Remington: The Science And Practice Of Pharmacy" Mack Publishing Co., Easton, PA, 19$^{th}$ Edition, (1995) (hereafter, Remington '95), or "Remington: The Science And Practice Of Pharmacy", Pharmaceutical Press, Easton, PA, 22$^{nd}$ Edition, (2013) (hereafter, Remington 2013), the contents of which are incorporated herein by reference in their entirety.

In certain embodiments, a pharmaceutical composition comprises a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a composition, pharmaceutical composition or compound of the invention is substantially free of contaminants (e.g., blood cells, platelets, polypeptides, minerals, blood-borne compounds or chemicals, virus, bacteria, other pathogens, toxin, and the like). In some embodiments a composition, pharmaceutical composition or compound of the invention is substantially free of serum and serum contaminants (e.g., serum proteins, serum lipids, serum carbohydrates, serum antigens and the like). In some embodiments a composition, pharmaceutical composition or compound of the invention is substantially free of a pathogen (e.g., a virus, parasite or bacteria). In some embodiments a composition, pharmaceutical composition or compound of the invention is substantially free of endotoxin. In some embodiments a composition, pharmaceutical composition or compound of the invention is sterile. In certain embodiments, a composition or pharmaceutical composition disclosed herein comprises a compound of Formula I, II, III or IV.

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), DMSO, combinations thereof and the like). In certain embodiments, reconstituted forms of a lyophilized pharmaceutical composition are suitable for parenteral administration (e.g., intravenous administration) to a mammal.

In certain embodiments, a pharmaceutical composition is configured for oral administration and may be formulated as a tablet, microtablet, minitablets, micropellets, powder, granules, capsules (e.g., capsules filled with microtablets, micropellets, powders or granules), emulsions, solutions, the like or combinations thereof. Pharmaceutical compositions configured for oral administration may comprise suitable coatings to delay or sustain release of the active ingredient, non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a compound of the invention from a topical patch.

In certain embodiments, an optimal pharmaceutical composition is determined by one skilled in the art depending upon, for example, on the intended route of administration, delivery format and desired dosage (see e.g., Remington '95 or Remington 2013, supra). A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Route of Administration

Any suitable method of administering a composition, pharmaceutical composition or compound of the invention to a subject can be used. Any suitable formulation and/or route of administration can be used for administration of a compound of the invention or composition disclosed herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's risk, age, and/or condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof. In some embodiments, a compound or composition disclosed herein is configured for oral administration. In some embodiments, a compound or composition disclosed herein is administered orally.

In some embodiments a compound of the invention or pharmaceutical composition described herein is administered to the lungs, bronchial passages, trachea, esophagus, sinuses, or nasal passages using a suitable method, non-limiting examples of which include intranasal administration, intratracheal instillation, and oral inhalative administration (e.g., by use of an inhaler, e.g., single/-multiple dose dry powder inhalers, nebulizers, and the like).

In some embodiments a compound of the invention or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, intravenously or by way of an inhaler, for example.

Alternately, one can administer a compound of the invention or composition in a local rather than systemic manner, for example, via direct application to the skin, mucous membrane or region of interest for treating, including using a depot or sustained release formulation.

In certain embodiments a pharmaceutical composition comprising a compound of the invention is administered alone (e.g., as a single active ingredient (AI or e.g., as a single active pharmaceutical ingredient (API)). In other embodiments, a pharmaceutical composition comprising a compound of the invention is administered in combination with one or more additional AIs/APIs, for example, as two separate compositions or as a single composition where the one or more additional AIs/APIs are mixed or formulated together with a compound of the invention in a pharmaceutical composition.

Dose and Therapeutically Effective Amount

In some embodiments, an amount of a compound of the invention (e.g., in a pharmaceutical composition) is a therapeutically effective amount. In certain embodiments, a pharmaceutical composition comprises a therapeutically effective amount of a compound disclosed herein. In some embodiments, a therapeutically effective amount of a compound of the invention is administered to a subject. In some embodiments, a therapeutically effective amount of a compound of the invention is an amount needed to obtain an effective therapeutic outcome. In certain embodiments, a therapeutically effective amount of a compound of the invention is an amount sufficient to treat and/or prevent obesity, assist a subject in weight loss, induce weight loss, suppress apatite, and/or inhibit weight gain in a subject, as contemplated herein. Determination of a therapeutically effective amount is well within the capability of those skilled in the art, especially in light of the detailed disclosure provided herein.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a compound of the invention may vary from subject to subject, often depending on age, weight, general health condition of a subject, severity of a obesity, and/or a particular combination of drugs being administered to a subject. Thus, in some embodiments, a therapeutically effective amount is determined empirically. Accordingly, a therapeutically effective amount of a compound or composition can be determined by one of ordinary skill in the art based on amounts found effective in animal or clinical studies, a physician's experience, and/or suggested dose ranges or dosing guidelines, for example.

In certain embodiments, a therapeutically effective amount of a compound of the invention is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a compound of the invention comprises one or more doses selected from at least 0.01 mg/kg (e.g., mg of a compound of the invention per kg body weight of a subject), at least 0.1 mg/kg, at least 0.5 mg/kg, at least 1 mg/kg, at least 10 mg/kg or at least 100 mg/kg. In certain embodiments, a therapeutically effective amount of a compound of the invention is selected from one or more doses of about 0.001 mg/kg (e.g., mg of a compound of the invention per kg body weight of a subject) to about 5000 mg/kg, 0.1 mg/kg to 5000 mg/kg, 1 mg/kg to 5000 mg/kg, 10 mg/kg to 5000 mg/kg, 0.01 mg/kg to 1000 mg/kg, 0.1 mg/kg to 1000 mg/kg, 1 mg/kg to 1000 mg/kg, 10 mg/kg to 1000 mg/kg, 100 mg/kg to 1000 mg/kg, 0.01 mg/kg to 500 mg/kg, 0.1 mg/kg to 500 mg/kg, 1 mg/kg to 500 mg/kg, 0.1 mg/kg to 250 mg/kg, 0.1 mg/kg to 150 mg/kg, 0.1 mg/kg to 100 mg/kg, 1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, 0.5 mg/kg to 5 mg/kg, intervening amounts and combinations thereof. In some aspects a therapeutically effective amount of a compound of the invention administered to a subject comprises one or more doses of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 50 mg/kg, 100 mg/kg, 500 mg/kg, and intervening amounts and combinations thereof. In some embodiments a therapeutically effective amount of a compound of the invention is between about 0.1 mg/kg and about 50 mg/kg.

In some embodiments a compound of the invention, or a pharmaceutical composition disclosed herein, is administered at a suitable frequency or interval as needed to obtain an effective therapeutic outcome. In some embodiments administering a therapeutically effective amount of a compound of the invention or a pharmaceutical composition disclosed herein comprises administering a suitable dose hourly, every two hours, every 4 hours, every 6 hours, three times a day, twice a day, once a day, six times a week, five times a week, four times a week, three times a week, twice a week, weekly, at combinations thereof, and/or at regular or irregular intervals thereof, and/or simply at a frequency or interval as needed or recommended by a medical professional. In some embodiments, a therapeutically effective amount of a compound of the invention, or a pharmaceutical composition disclosed herein, is administered continuously, for example by intravenous administration over a suitable period of time. In some embodiments, a compound of the invention is administered for a period of 1 to 30 days, 1 to 52 weeks, 1 to 5 years, or other suitable periods of time. In some embodiments, a compound of the invention is administered until a subject attains a suitable healthy body mass index (BMI), which can be determined by a medical professional. In some embodiments, a compound of the invention is administered until a subject attains a BMI of 18.5 to 25 or a BMI of 18.5 to 29. In certain embodiments, administering a therapeutically effective amount of a compound of the invention comprises administering a dose of about 1 to 1000 mg/kg, about 1 to 100 mg/kg or about 1 to 30 mg/kg administered at a frequency of once per day.

In some embodiments a therapeutically effective amount of a compound of the invention is administered to a subject prior to, during and/or after exercise. In some embodiments a therapeutically effective amount of a compound of the invention is administered to a subject up to 1 day prior to, up to 20 hours prior to, up to 15 hours prior to, up to 10 hours prior to, up to 5 hours prior to, up to 2 hours prior to or up to 1 hour prior to exercise or strenuous activity. In some embodiments a therapeutically effective amount of a compound of the invention is administered to a subject 0 to 72 hours, 0 and 48 hours, 0 to 24 hours, 0 to 12 hours, 0 to 6 hours, 0 to 4 hours, or 0 to 2 hours before exercise or strenuous activity. In some embodiments a therapeutically effective amount of a compound of the invention is administered during exercise or strenuous activity. In some embodiments a therapeutically effective amount of a compound of the invention is administered intermittently or continuously for up to 1 hour after, 2 hours after, 4 hours after, 6 hours after, 12 hours after, 24 hours after, 2 days after, 3 days after, a week after, 1 month after, 3 months after, 6 months after, 12 months after, 18 months after, 24 months after or up to 36 months after exercise or strenuous activity.

Kits

In some embodiments, provided herein is a kit comprising a compound of the invention or a pharmaceutical composition comprising a compound of the invention. In some embodiments, a kit comprises one or more doses of a pharmaceutical composition comprising a compound of the invention. In some embodiments, a kit comprises one or more packs and/or one or more dispensing devices, which can contain one or more doses of a compound of the invention, or pharmaceutical composition thereof, as described herein. Non-limiting examples of a pack include a metal, glass, or plastic container, syringe or blister pack that comprises a compound of the invention or a composition described herein. In certain embodiments, a kit comprises a dispensing device such as a syringe or inhaler, that may or may not comprise a compound of the invention or a composition described herein. A pack and/or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a compound of the invention sufficient to treat a patient for 1 day to 1 year, 1 day to 180 days, 1 day to 120 days, 1 day to 90 days, 1 day to 60 days, 1 day to 30 days, 1-24 hours, 1-12 hours, 1-4 hours, or amount of time there between.

A kit optionally includes a product label and/or one or more packaging inserts, that provide a description of the components or instructions for use in vitro, in vivo, or ex vivo, of the components therein. Exemplary instructions include instructions for a treatment protocol or therapeutic regimen. In certain embodiments, a kit comprises packaging material, which refers to a physical structure housing components of the kit. The packaging material can maintain the components sterilely, and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory-type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. A kit can additionally include labels or instructions for practicing any of the methods described herein. Product labels or inserts can include information on potential adverse side effects and/or warnings.

EXAMPLES

Example 1

J147 or vehicle was administered once daily to Sprague-Dawley rats via oral gavage for 28 consecutive days at a daily dose of 0, 30, 100 or 300 mg/kg. J174 was prepared in a vehicle formulation comprising 5% ethanol, 5% DMSO and 90% corn oil (v/v/v). Certified rodent diet and water was available ad libitum. Groups 1-4 contained 10 animals/sex/group. Groups 1 (control) and 4 (high dose) also included an additional 5 animals/sex/group for use as recovery animals. The recovery animals were maintained on study for a 14-day postdosing recovery period. Animals in Groups 1-4 were monitored for morbidity and mortality, clinical signs, detailed clinical observations, body weight, food consumption, ophthalmologic parameters, neurobehavioral assessment consisting of a Functional Observational Battery (FOB) and a motor activity test, hematology, coagulation, serum chemistry, and urinalysis parameters. Postmortem assessment included necropsy, measurement of selected organ weights, and microscopic evaluation of a standard set of tissues. Plasma samples for bioanalysis were collected on Days 1 and 28 from satellite toxicokinetic animals in Groups 5 through 8. Animals in these groups were euthanized following the last blood sampling and carcasses were discarded without examination. The study protocol is shown below in Table 1.

TABLE 1

| Group | Dose (mg/kg/day) | Dose Volume (mL/kg) | Dose Concentrations (mg/ml) | No. of Animals | No. Animals terminated at day 29 | No. of Recovery Animals terminated at day 43 |
| --- | --- | --- | --- | --- | --- | --- |
| 1 | 0 | 5 | 0 | 15 | 10 | 5 |
| 2 | 30 | 5 | 6 | 10 | 10 | 0 |
| 3 | 100 | 5 | 20 | 10 | 10 | 0 |
| 4 | 300 | 5 | 60 | 15 | 10 | 5 |
| 5 | 0 | 5 | 0 | 3 | 3* | 0 |
| 6 | 30 | 5 | 6 | 9 | 9* | 0 |
| 7 | 100 | 5 | 20 | 9 | 9* | 0 |
| 8 | 300 |  | 60 | 9 | 9* | 0 |

Groups 1-4 = Toxicity Groups
Groups 5-8 = Toxicokinetic Groups
Toxicity females dosed one day later than Toxicity males and Toxicokinetic males/females (staggered start).
*Termination on these days for TK animals, no gross necropsies.

Detailed Results

Body Weights

Mean Body Weights are shown in Table 2 (Males) and Table 3 (Females).

TABLE 2

Mean Body Weights-Males
Bodyweight (g)

| Sex: Male | | Day(s) Relative to Start Date | | | | | |
|---|---|---|---|---|---|---|---|
| | | −2 | −1 | 7 aa[1] | 14 aa[1] | 21 aa[1] | 28 aa[1] |
| Group 1- | Mean | 279.19 | 288.71 | 344.68 | 394.51 | 432.15 | 464.15 |
| 0 mg/kg | SD | 8.85 | 8.69 | 14.55 | 19.60 | 23.06 | 27.04 |
| | N | 15 | 15 | 15 | 15 | 15 | 15 |
| Group 2- | Mean | 278.60 | 285.27 | 338.91 | 391.29 | 430.90 | 465.41 |
| 30 mg/kg | SD | 8.00 | 9.38 | 12.93 | 19.28 | 26.18 | 30.35 |
| | N | 10 | 10 | 10 | 10 | 10 | 10 |
| Group 3- | Mean | 278.57 | 286.67 | 335.34 | 376.48 | 409.98 | 436.87 |
| 100 mg/kg | SD | 8.78 | 9.34 | 12.07 | 17.77 | 22.09 | 28.03 |
| | N | 10 | 10 | 10 | 10 | 10 | 10 |
| Group 4- | Mean | 278.97 | 287.50 | 321.93 dd[2] | 350.83 dd[2] | 372.04 dd[2] | 388.75 dd[2] |
| 300 mg/kg | SD | 8.29 | 8.80 | 17.30 | 23.80 | 29.24 | 34.05 |
| | N | 15 | 15 | 15 | 15 | 15 | 15 |

Statistical Test: Anova & Dunnett's Test
[1] [aa-Statistical Test: Analysis of Variance $p < 0.01$]
[2] [dd-Statistical Test: Dunnett 2 Sided $p < 0.01$]

| Sex: Male | | Day(s) Relative to Start Date | |
|---|---|---|---|
| | | 35 aa[1] | 42 a[2] |
| Group 1- | Mean | 491.64 | 513.56 |
| 0 mg/kg | SD | 36.79 | 46.08 |
| | N | 5 | 5 |
| Group 4- | Mean | 415.68 dd[3] | 446.14 d[4] |
| 300 mg/kg | SD | 24.30 | 22.39 |
| | N | 5 | 5 |

Statistical Test: Anova & Dunnett's Test
[1] [aa-Statistical Test: Analysis of Variance $p < 0.01$]
[2] [a-Statistical Test: Analysis of Variance $p < 0.051$]
[3] [dd-Statistical Test: Dunnett 2 Sided $p < 0.05$]
[4] [d-Statistical Test: Dunnett 2 Sided $p < 0.01$]

TABLE 3

Mean Body Weights-Females
Bodyweight (g)

| Sex: Female | | Day(s) Relative to Start Date | | | | | |
|---|---|---|---|---|---|---|---|
| | | −3 | −1 | 7 | 14 aa[1] | 21 aa[1] | 28 aa[1] |
| Group 1- | Mean | 200.39 | 205.14 | 223.79 | 239.60 | 250.88 | 251.74 |
| 0 mg/kg | SD | 8.26 | 7.78 | 11.09 | 11.00 | 11.93 | 12.04 |
| | N | 15 | 15 | 15 | 15 | 15 | 15 |
| Group 2- | Mean | 200.70 | 203.02 | 220.64 | 233.70 | 243.15 | 248.23 |
| 30 mg/kg | SD | 8.35 | 9.43 | 12.78 | 16.39 | 18.24 | 17.98 |
| | N | 10 | 10 | 10 | 10 | 10 | 10 |
| Group 3- | Mean | 201.20 | 206.05 | 215.78 | 225.77 d[2] | 232.79 d[2] | 234.39 |
| 100 mg/kg | SD | 7.68 | 11.15 | 12.86 | 12.96 | 12.92 | 15.09 |
| | N | 10 | 10 | 10 | 10 | 10 | 10 |
| Group 4- | Mean | 200.70 | 207.85 | 214.74 | 222.99 dd[3] | 228.03 dd[3] | 220.53 dd[3] |
| 300 mg/kg | SD | 7.88 | 5.61 | 11.75 | 13.58 | 17.99 | 23.10 |
| | N | 15 | 15 | 15 | 15 | 15 | 15 |

Statistical Test: Anova & Dunnett's Test
[1] [aa-Statistical Test: Analysis of Variance $p < 0.01$]
[2] [d-Statistical Test: Dunnett 2 Sided $p < 0.051$]
[3] [dd-Statistical Test: Dunnett 2 Sided $p < 0.01$]

TABLE 3-continued

| | | Mean Body Weights-Females Bodyweight (g) | |
|---|---|---|---|
| | | Day(s) Relative to Start Date | |
| Sex: Female | | 35 | 42 |
| Group 1- 0 mg/kg | Mean | 267.22 | 275.68 |
| | SD | 11.57 | 9.93 |
| | N | 5 | 5 |
| Group 4- 300 mg/kg | Mean | 249.62 | 258.24 |
| | SD | 15.18 | 24.27 |
| | N | 5 | 5 |

Statistical Test: Anova & Dunnett's Test

Mean Body Weight Gain is shown in Table 4 (Males) and Table 5 (Females).

TABLE 4

| | | Mean Body Weight Gain-Males Bodyweight Gain (g) | | | | | |
|---|---|---|---|---|---|---|---|
| | | Day(s) Relative to Start Date | | | | | |
| Sex: Male | | $-1 \rightarrow 7$ aa[1] | $7 \rightarrow 14$ aa[1] | $14 \rightarrow 21$ aa[1] | $21 \rightarrow 28$ aa[1] | $-1 \rightarrow 28$ aa[1] | $28 \rightarrow 42$ |
| Group 1- 0 mg/kg | Mean | 55.97 | 49.83 | 37.65 | 32.00 | 175.44 | 47.60 |
| | SD | 7.51 | 7.17 | 5.01 | 6.28 | 22.05 | 13.82 |
| | N | 15 | 15 | 15 | 15 | 15 | 5 |
| Group 2- 30 mg/kg | Mean | 53.64 | 52.38 | 39.61 | 34.51 | 180.14 | — |
| | SD | 6.23 | 7.11 | 8.36 | 6.43 | 23.38 | — |
| | N | 10 | 10 | 10 | 10 | 10 | — |
| Group 3- 100 mg/kg | Mean | 48.67 | 41.14 d[2] | 33.50 | 26.89 | 150.20 | — |
| | SD | 9.50 | 7.96 | 8.10 | 7.41 | 27.27 | — |
| | N | 10 | 10 | 10 | 10 | 10 | — |
| Group 4- 300 mg/kg | Mean | 34.43 dd[3] | 28.89 dd[3] | 21.21 dd[3] | 16.71 dd[3] | 101.25 dd[3] | 50.60 |
| | SD | 11.31 | 8.62 | 7.84 | 6.76 | 29.54 | 3.47 |
| | N | 15 | 15 | 15 | 15 | 15 | 5 |

Statistical Test: Anova & Dunnett's Test
[1][aa-Statistical Test: Analysis of Variance $p < 0.01$]
[2][d-Statistical Test: Dunnett 2 Sided $p < 0.051$]
[3][dd-Statistical Test: Dunnett 2 Sided $p < 0.01$]

TABLE 5

| | | Mean Body Weight Gain-Females Bodyweight (g) | | | | | |
|---|---|---|---|---|---|---|---|
| | | Day(s) Relative to Start Date | | | | | |
| Sex: Female | | $-1 \rightarrow 7$ aa[1] | $7 \rightarrow 14$ aa[1] | $14 \rightarrow 21$ aa[1] | $21 \rightarrow 28$ aa[1] | $-1 \rightarrow 28$ aa[1] | $28 \rightarrow 42$ |
| Group 1- 0 mg/kg | Mean | 18.65 | 15.81 | 11.28 | 0.86 | 46.60 | 23.10 |
| | SD | 7.98 | 7.40 | 4.48 | 6.44 | 7.78 | 6.67 |
| | N | 15 | 15 | 15 | 15 | 15 | 5 |
| Group 2- 30 mg/kg | Mean | 17.62 | 13.06 | 9.45 | 5.08 | 45.21 | — |
| | SD | 4.47 | 5.61 | 6.01 | 6.07 | 9.21 | — |
| | N | 10 | 10 | 10 | 10 | 10 | — |
| Group 3- 100 mg/kg | Mean | 9.73 d[3] | 9.99 d[3] | 7.02 | 1.60 | 28.34 dd[4] | — |
| | SD | 5.34 | 4.84 | 5.08 | 6.76 | 9.89 | — |
| | N | 10 | 10 | 10 | 10 | 10 | — |
| Group 4- 300 mg/kg | Mean | 6.89 dd[4] | 8.25 dd[4] | 5.03 dd[4] | −7.49 d[3] | 12.68 dd[4] | 32.82 |
| | SD | 8.81 | 4.61 | 6.25 | 9.84 | 19.91 | 16.15 |
| | N | 15 | 15 | 15 | 15 | 15 | 5 |

Statistical Test: Anova & Dunnett's Test
[1][aa-Statistical Test: Analysis of Variance $p < 0.01$]
[2][a-Statistical Test: Analysis of Variance $p < 0.051$]
[3][d-Statistical Test: Dunnett 2 Sided $p < 0.05$]
[4][dd-Statistical Test: Dunnett 2 Sided $p < 0.01$]

TABLE 6

Terminal Mean Body Weights

| Group/Sex | Terminal Body Weight (g) | % Diff from Control | Group/Sex | Terminal Body Weight (g) | % Diff from Control |
|---|---|---|---|---|---|
| 1M | 437.37 | — | 1F | 243.96 | — |
| 2M | 443.50 | +1.4 | 2F | 238.10 | -2.4 |
| 3M | 412.50 | -5.69 | 3F | 225.43 | -7.6 |
| 4M | 359.05 | -17.91 | 4F | 209.24 | -14.23 |

Compared to Group 1 controls, group mean body weight in males was decreased 5.9 and 16.2% at 100 and 300 mg/kg/day males on Day 28. Compared to Group 1 controls, group mean body weight in females was decreased 6.9 and 12.4% at 100 and 300 mg/kg/day for females on Day 28. Group mean weight gain from Day -1 to 28 for males in Groups 1 and 2 was 175 and 180 grams, respectively, while mean body weight gains for Group 3 and 4 males was 150 and 101 grams, respectively.

Group mean weight gain from Day -1 to 28 for females in Groups 1 and 2 was 47 and 45 grams, respectively while mean body weight gains for Groups 3 and 4 females were 28 and 13 grams, respectively.

These alterations in body weight and body weight gain were often statistically significant, particularly at the high dose level, and were considered related to test article exposure.

During the recovery period, group mean body weight gain for both males and females at 300 mg/kg/day exceeded that seen in the vehicle-treated controls. Full recovery of body weight and body weight gain was seen during the recovery period.

Food Consumption

Mean Food Consumption is shown in Table 7 (Males) and Table 8 (Females).

TABLE 7

Mean Food Consumption-Males

| Sex: Male | | $-1 \to 7$ aa[1] | $7 \to 14$ aa[1] | $14 \to 21$ aa[1] | $21 \to 28$ aa[1] | $28 \to 35$ | $35 \to 42$ |
|---|---|---|---|---|---|---|---|
| Group 1- 0 mg/kg | Mean | 24.42 | 25.36 | 25.48 | 24.96 | 27.01 | 29.21 |
| | SD | 1.89 | 2.21 | 1.90 | 2.09 | 2.14 | 2.83 |
| | N | 15 | 15 | 15 | 15 | 5 | 5 |
| Group 2- 30 mg/kg | Mean | 23.90 | 24.85 | 25.03 | 25.13 | — | — |
| | SD | 1.44 | 1.79 | 2.46 | 2.40 | — | — |
| | N | 10 | 10 | 10 | 10 | — | — |
| Group 3- 100 mg/kg | Mean | 23.68 | 21.47 dd[2] | 23.65 | 23.73 | — | — |
| | SD | 2.11 | 3.57 | 2.44 | 2.38 | — | — |
| | N | 10 | 10 | 10 | 9 | — | — |
| Group 4- 300 mg/kg | Mean | 19.83 dd[2] | 20.24 dd[2] | 21.50 dd[2] | 20.78 dd[2] | 26.98 | 28.99 |
| | SD | 2.66 | 2.81 | 3.26 | 2.13 | 1.89 | 2.17 |
| | N | 15 | 15 | 15 | 15 | 5 | 5 |

Statistical Test: Anova & Dunnett's Test
[1][aa-Statistical Test: Analysis of Variance p < 0.01]
[2][dd-Statistical Test: Dunnett 2 Sided p < 0.01]

TABLE 8

Mean Food Consumption-Females
Food Mean Consumption (g/animal/day)

| Sex: Female | | $-1 \to 7$ aa[1] | $7 \to 14$ aa[1] | $14 \to 21$ | $21 \to 28$ a[2] | $28 \to 35$ a[2] | $35 \to 42$ |
|---|---|---|---|---|---|---|---|
| Group 1- 0 mg/kg | Mean | 16.23 | 15.52 | 16.34 | 15.29 | 18.86 | 18.77 |
| | SD | 1.12 | 1.53 | 1.77 | 1.06 | 2.37 | 1.40 |
| | N | 15 | 14 | 13 | 13 | 5 | 5 |
| Group 2- 30 mg/kg | Mean | 15.49 | 14.89 | 15.47 | 15.12 | — | — |
| | SD | 1.12 | 1.12 | 1.19 | 1.24 | — | — |
| | N | 9 | 10 | 10 | 10 | — | — |
| Group 3- 100 mg/kg | Mean | 14.33 dd[3] | 13.85 d[4] | 14.70 | 13.98 | — | — |
| | SD | 1.24 | 1.42 | 1.73 | 1.18 | — | — |
| | N | 10 | 10 | 10 | 10 | — | — |
| Group 4- 300 mg/kg | Mean | 13.75 dd[3] | 13.81 dd[3] | 14.73 | 12.91 d[4] | 22.30 d[4] | 20.22 |
| | SD | 2.01 | 1.33 | 2.46 | 1.63 | 1.63 | 2.05 |
| | N | 15 | 15 | 15 | 15 | 5 | 5 |

Statistical Test: Anova & Dunnett's Test
[1][aa-Statistical Test: Analysis of Variance p < 0.01]
[2][a-Statistical Test: Analysis of Variance p < 0.051]
[3][dd-Statistical Test: Dunnett 2 Sided p < 0.01]
[4][d-Statistical Test: Dunnett 2 Sided p < 0.05]

Food consumption was decreased at 100 and 300 mg/kg/day in both sexes compared to Group 1 controls. Food consumption decreases at 300 mg/kg/day in both sexes were often statistically significant and at 100 mg/kg/day were sometimes statistically significant. Compared to Group 1 controls, group mean food consumption from Days 21 to 28 in males was decreased 4.9 and 16.7% at 100 and 300 mg/kg/day, respectively. Compared to Group 1 controls, group mean food consumption from Days 21 to 28 in females was decreased 8.6 and 15.6% at 100 and 300 mg/kg/day, respectively.

These alterations in food consumption were considered related to test article exposure.

Group mean food consumption during the recovery period was similar between the vehicle-treated control and 300 mg/kg/day animals indicating full recovery of food consumption during the recovery period.

Summary of Results and Discussion

Dose formulation analysis showed formulations were accurately prepared, homogenous, and stable for the duration of use. Incurred sample re-analysis (ISR) of bioanalytical plasma samples did not pass acceptance criteria. Additionally, analysis of Day 28 samples also occurred outside the known long-term stability (LTS) range of the validated bioanalytical method. Thus, the bioanalytical and toxicokinetic results for J147 are considered to be for information only. The bioanalytical and toxicokinetic analysis results should also be considered in light of the fact that Day 28 samples were analyzed outside of their LTS.

Noteworthy clinical observations during the 28-day treatment period were confined to soft feces noted in some animals of both sexes at 300 mg/kg/day. Body weight, body weight gain, and food consumption were decreased at 100 and 300 mg/kg/day in both sexes. A general decrease in activity was noted as evidenced by decreased distance traveled, ambulatory time, horizontal counts, vertical counts, and vertical breaks, and an increase in resting time in the motor activity portion of the Functional Observational Battery (FOB) conducted on Day 1. These alterations were evident in males at all dose levels and in females at 100 and 300 mg/kg/day. While treatment-related, these neurobehavioral findings were not considered adverse. There were no noteworthy clinical observations during the recovery period, and J147-related effects on body weight and food consumption were reversible following cessation of treatment. At the end of the 28-day treatment period, mean red blood cell counts, hematocrit, and hemoglobin values were decreased in males at all dose levels and in females at 100 and 300 mg/kg/day. Mean platelet and reticulocyte counts were increased at all dose levels in both sexes. Prothrombin time was decreased in both sexes at all dose levels. Decreased mean serum glucose concentrations were noted in males at 100 mg/kg/day and in both sexes at 300 mg/kg/day. Decreased mean serum triglyceride concentrations were noted in males at 100 and 300 mg/kg/day. Effects on serum glucose and triglyceride concentrations were considered secondary to decreased food consumption during the treatment period. Urinalysis revealed increased levels of urinary ketones in males at 300 mg/kg/day. There were no anatomic pathology correlates to these clinical pathology findings. At the end of the 14-day recovery period, test article-related effects on serum triglyceride concentrations and red cell mass persisted in animals previously administered 300 mg/kg/day J147 for 28 days.

There were no alterations noted at 30 mg/kg/day which were considered related to test article administration. Decreased activity as seen in the motor activity test of the FOB, and increased platelet and reticulocyte counts seen at this dose level, were not considered adverse findings. Though there were indicators of decreased activity in the FOB, decreased activity was never called at any dose level as a clinical observation and, with the exception of a few instances of hair loss, there were no clinical observations of any sort at 30 mg/kg/day. The increases in platelet counts at 30 mg/kg/day in females was small (3.8%) and in males the increases were not dose proportional. The increased reticulocyte counts were considered an adaptive response to the decreases in RBC parameters.

At the terminal necropsy, enlarged liver and small thymus were seen in one or two animals at 300 mg/kg/day. Group mean liver weights were increased in males at all dose levels and in females at 100 and 300 mg/kg/day. Decreases in group mean thymus weights were seen in both sexes at 100 and 300 mg/kg/day. Microscopically, subacute perivascular inflammation was noted in the liver of both sexes at 300 mg/kg/day, and hepatocellular hypertrophy was seen in both sexes at 100 and 300 mg/kg/day. The incidence of single cell necrosis of acinar cells in the pancreas was increased at 300 mg/kg/day in both sexes and increased in males at 100 mg/kg/day. Additionally, thymic lymphoid depletion was noted in both sexes at 300 mg/kg/day. Findings of increased liver weight and hepatocellular hypertrophy were considered to represent an adaptive response rather than an adverse or toxicological effect. There were no J147-related organ weight, macroscopic or microscopic findings in high-dose (300 mg/kg/day) animals on Day 43 following a 2-week treatment-free recovery period.

CONCLUSION

Accurate measures of test article exposure were not available as the toxicokinetic data were considered in light of the fact that plasma sample incurred sample re-analysis did not meet acceptance criteria and Day 28 samples were analyzed outside their long-term stability window. Given that there was clear evidence of toxicity at the mid and high dose groups, the Study Director believes that this study met the objective of examining the toxicity profile of J147. The study did not meet the objective of examining the toxicokinetic profile of J147 following oral exposure. Under the conditions of this study, the no-observed-adverse-effect-level (NOAEL) for J147 was considered to be 30 mg/kg/day. Day 1 Cmax and AUC0-last values at the NOAEL were 146 ng/mL and 835 hr*ng/mL, respectively, in males and 50.8 ng/mL and 233 hr*ng/mL, respectively, in females. Cmax and AUC0-last values should be considered in light of the caveats mentioned in the preceding paragraph. The lowest-observed-adverse-effect-level (LOAEL) is 100 mg/kg/day in both sexes based on test article-related decreases in body weight/body weight gain and food consumption, decreased activity, decreases in measures of red blood cell mass, decreased prothrombin time, decreased serum glucose and triglycerides, decreased thymus weights, and single cell necrosis of pancreatic acinar cells in males.

Example 2

J147 or vehicle was administered once daily to beagle dogs via oral gavage for up to 28 days at a daily dose of 0, 30, 100 and 300 mg/kg. J174 was prepared in a vehicle formulation comprising 5% ethanol, 5% DMSO and 90% corn oil (v/v/v). Block Lab Diet (Certified Canine Diet #5007, PMI Nutrition International, Inc.) was offered via limited feedings, except during designated periods. The animals were offered food 2 hours post-dose on each dosing day for 2 to 5 hours. Food was offered 2 to 5 hours/day during the acclimation period and during the recovery period. Tap water was available ad libitum via an automatic watering system. The study protocol is shown below in Table 9.

TABLE 9

| Group | Dose (mg/kg/day) | Dose Volume (mL/kg) | Dose Concentrations (mg/ml) | No. of Animals |
|---|---|---|---|---|
| 1 | 0 | 2.5 | 0 | 6 |
| 2 | 30 | 2.5 | 12 | 4 |
| 3 | 100 | 2.5 | 40 | 4 |
| 4 | 300 | 2.5 | 120 | 6 |

Body weight and body weight gain were decreased in all J147-treated groups (both sexes) compared to the vehicle-treated control group. Day 28 group mean body weight values for males were decreased by 23% and 26% at 30 and 100 mg/kg/day, respectively. Group mean body weight for 300 mg/kg/day males on Day 22 was decreased 18% versus the Day 28 control value. Day 28 group mean body weight values for females were decreased by 19% and 21% at 30 and 100 mg/kg/day, respectively. Group mean body weight for 300 mg/kg/day females on Day 21 was decreased by 23% versus the Day 28 control value. High-dose (300 mg/kg/day) recovery animals (males and females) gained weight rapidly during the recovery period indicating full recovery of body weight and body weight gain during the 14-day recovery period.

Food consumption was decreased in all J147-treated groups (both sexes) compared to the vehicle-treated control group. Day 28 group mean food consumption values for males were decreased by 31% and 39% at 30 and 100 mg/kg/day, respectively. Group mean food consumption for 300 mg/kg/day males on Day 22 was decreased by 48% versus the Day 28 control value. Day 28 group mean food consumption values for females were decreased by 45% and 48% at 30 and 100 mg/kg/day, respectively. Group mean food consumption for 300 mg/kg/day females on Day 21 was decreased by 38% versus the Day 28 control value. High-dose (300 mg/kg/day) recovery animals (males and females) showed dramatic and immediate increases in food consumption during the recovery period, indicating rapid and full recovery of food consumption during the 14-day recovery period.

Example 3

J147 was administered once daily to beagle dogs via oral gavage for up to 28 days at a daily dose of 0, 1, 10 and 30 mg/kg. J174 was prepared in a vehicle formulation comprising 5% ethanol, 5% DMSO and 90% corn oil (v/v/v). Block Lab Diet (Certified Canine Diet #5007, PMI Nutrition International, Inc.) was offered via limited feedings, except during designated periods. The animals were offered food 2 hours postdose on each dosing day for 2 to 5 hours. Food was offered 2 to 5 hours/day during the acclimation period and during the recovery period. Tap water was available ad libitum via an automatic watering system. The study protocol is shown below in Table 10.

TABLE 10

Study Design

| Group | Dose (mg/kg/day) | Dose Volume (mL/kg) | Dose Concentrations (mg/ml) | No. of Male Animals | No. of Female Animals |
|---|---|---|---|---|---|
| 1 | 0 | 2.5 | 0 | 6 | 6 |
| 2 | 1 | 2.5 | 0.4 | 4 | 4 |
| 3 | 10 | 2.5 | 4 | 4 | 4 |
| 4 | 30 | 2.5 | 6 | 5 | 6 |

Figure 1D:
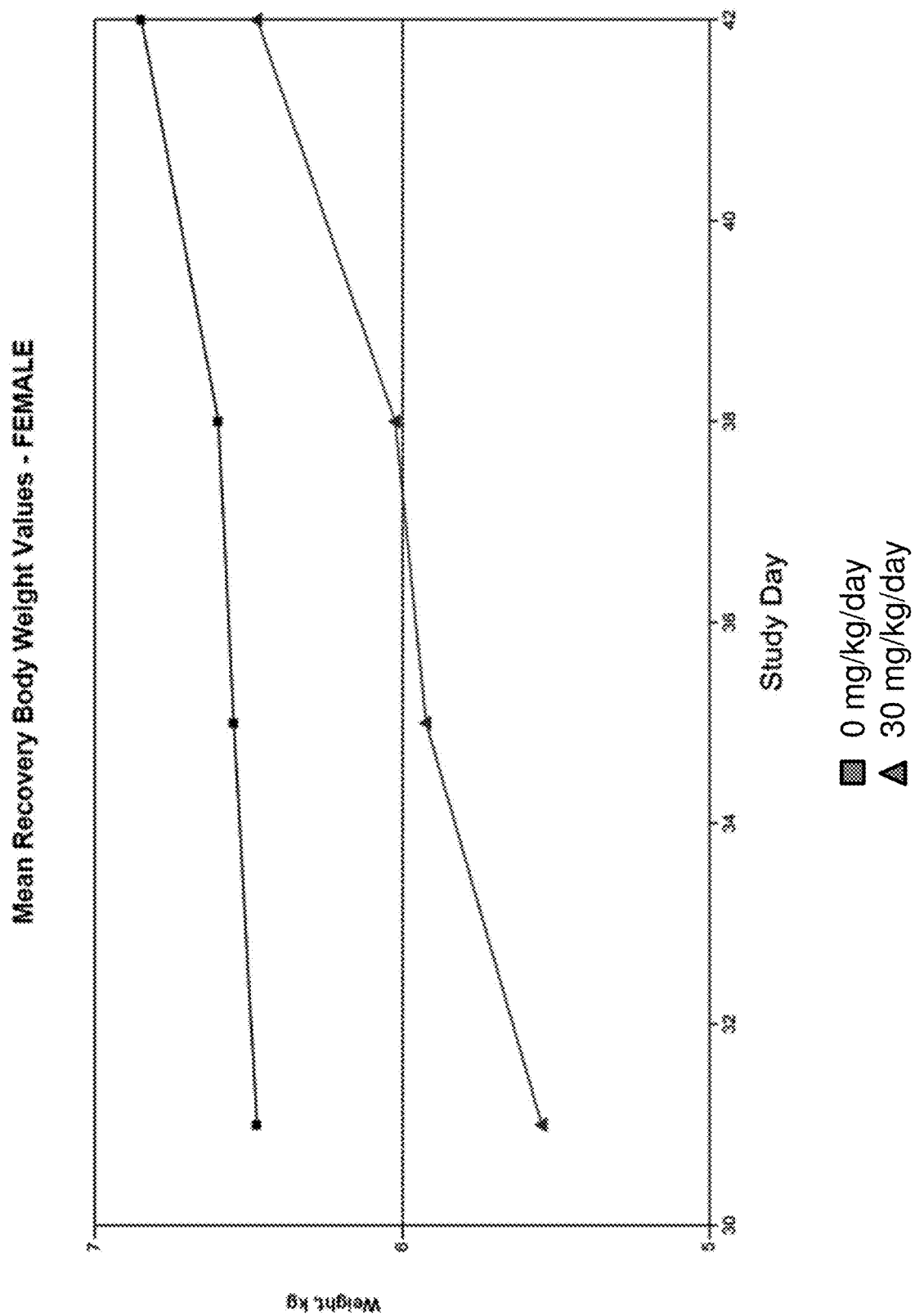
Figure 2A:
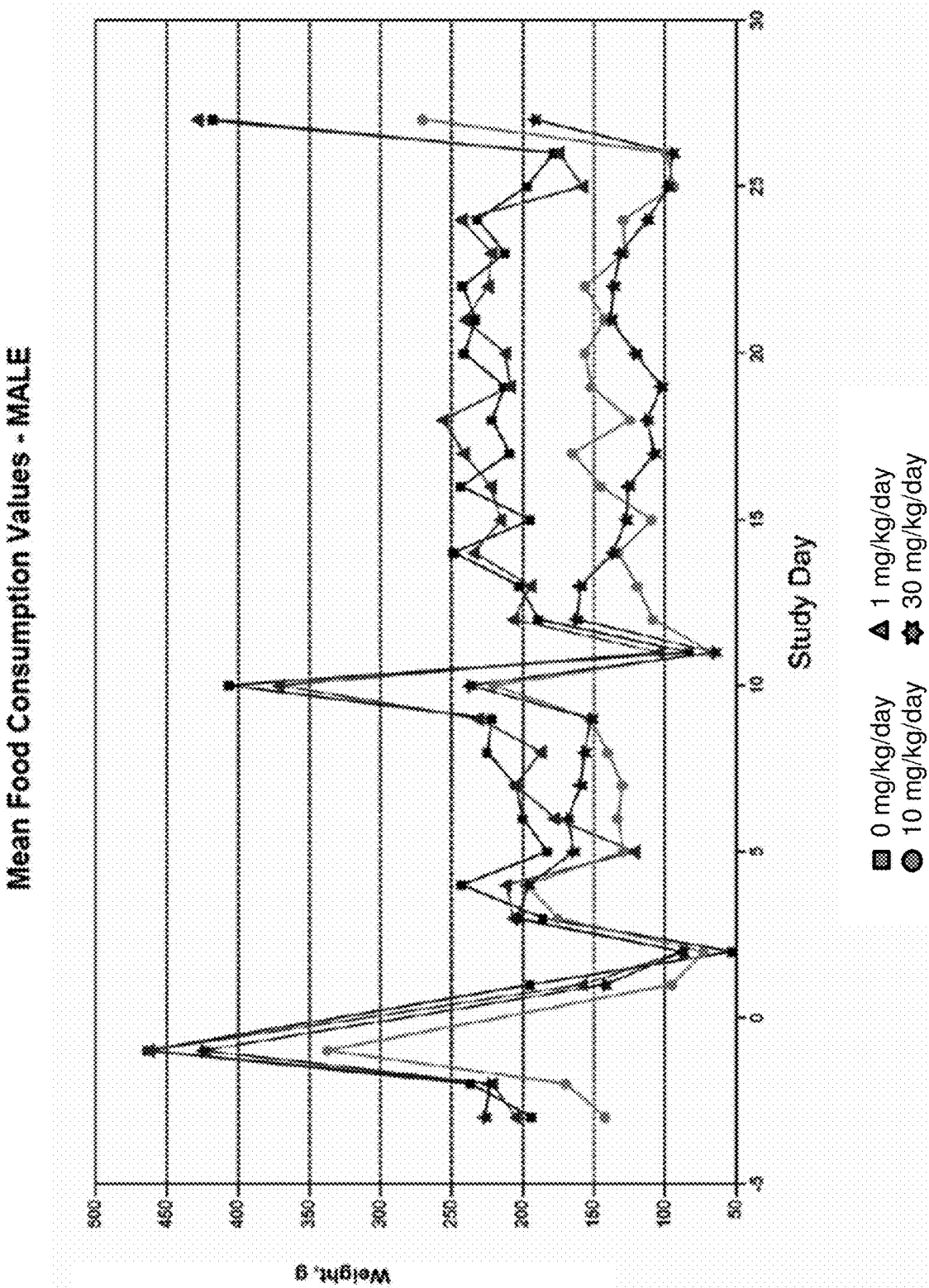
Figure 2C:
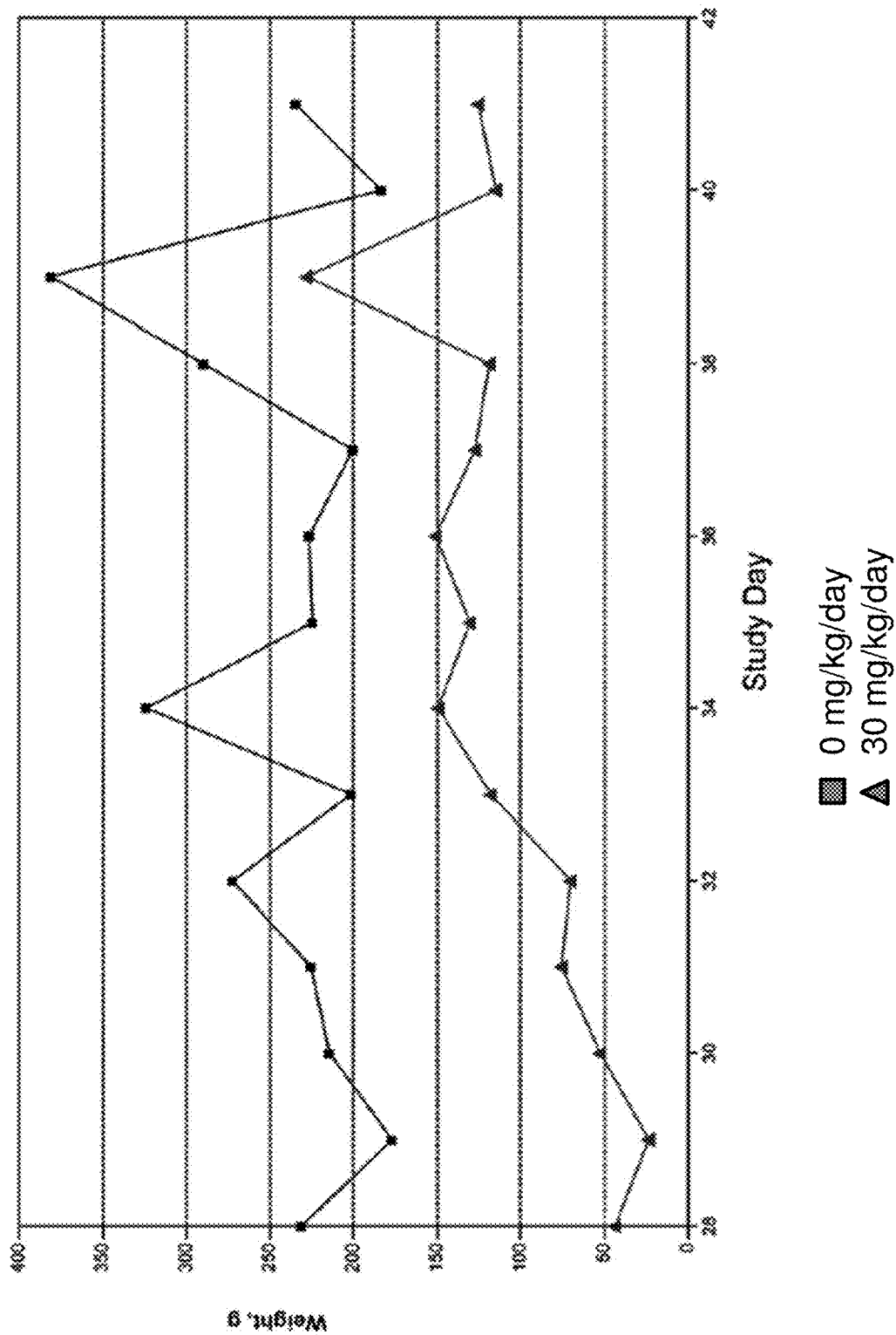
FIGS. 2C and 2D show a graphical representation of food consumption (Y-axis; grams/day) over time (x-axis; Study Days) of beagle dogs during the recovery period (i.e. after administration of final treatment) of dogs previously treated with J147 at 30 mg/kg/day (triangles) or with control (i.e., 0 mg/kg/day of J147; squares).
Figure 2D:
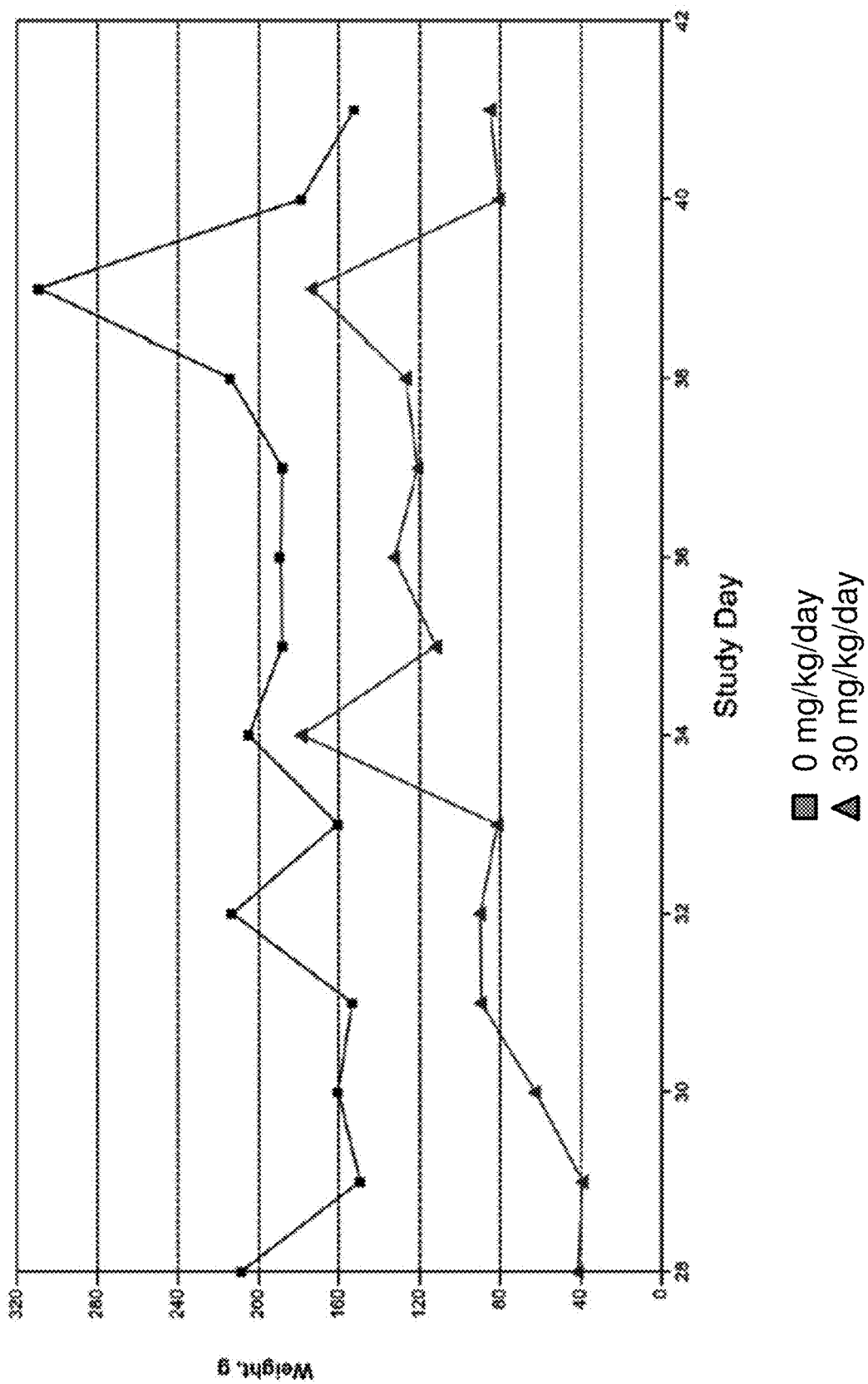

Body weight loss with lower food consumption was noted in Groups 3 and 4 at doses levels of 10 mg/kg/day and 30 mg/kg/day. At 10 mg/kg/day, 3 of 4 males and 4 of 4 females lost weight (up to −9% compared to pre-test levels). At 30 mg/kg/day, 5 of 6 males and 6 of 6 females lost weight (up to −12% and −17%, respectively, of pretest levels). The results are summarized in Table 11 (males), Table 12 (females), and FIGS. 1 and 2. Body weight gain during a 14-day recovery period was comparable to control values in both sexes at 30 mg/kg/day (e.g., see FIG. 1C and 1D). It was noted that although animals in Group 3 did only experience moderate weight loss, they did not experience the weight gain observed for the control animals of Group 1. Consequently, it was concluded the J147 induces weight loss and inhibits weight gain. This result may have been due, at least in part, to apatite suppression as observed in FIG. 2.

TABLE 11

MPI Research Study Number 2382-001
J147: A 28-Day Oral (Gavage) Toxicity Study in Beagle Dogs with a 14-Day Recovery Period
Summary of Body Weight Values-MALE

| Endpoint | Study Interval (Day) | 0 mg/kg/day | | | 1 mg/kg/day | | | 10 mg/kg/day | | | 30 mg/kg/day | | |
|---|---|---|---|---|---|---|---|---|---|---|---|---|---|
| | | Mean | SD | N | Mean | SD | N | Mean | SD | N | Mean | SD | N |
| Body Weight kg | −1 | 7.950 | 0.9466 | 6 | 7.813 | 0.4535 | 4 | 7.563 | 0.6060 | 4 | 7.908 | 0.5305 | 6 |
| | 3 | 7.983 | 0.8635 | 6 | 7.850 | 0.4916 | 4 | 7.588 | 0.7016 | 4 | 7.900 | 0.6245 | 6 |
| | 7 | 8.000 | 0.8614 | 6 | 7.838 | 0.4715 | 4 | 7.675 | 0.6764 | 4 | 7.933 | 0.6055 | 6 |
| | 10 | 8.175 | 0.8347 | 6 | 8.000 | 0.4340 | 4 | 7.763 | 0.7111 | 4 | 8.008 | 0.6719 | 6 |
| | 14 | 8.208 | 0.7677 | 6 | 8.000 | 0.5000 | 4 | 7.625 | 0.7751 | 4 | 7.967 | 0.7441 | 6 |
| | 17 | 8.300 | 0.7836 | 6 | 8.075 | 0.4924 | 4 | 7.563 | 0.9586 | 4 | 7.883 | 0.7885 | 6 |
| | 21 | 8.375 | 0.7961 | 6 | 8.200 | 0.5354 | 4 | 7.663 | 0.9656 | 4 | 7.800 | 0.7635 | 6 |
| | 24 | 8.467 | 0.7236 | 6 | 8.325 | 0.5331 | 4 | 7.638 | 0.9835 | 4 | 7.825 | 0.8785 | 6 |
| | 28 | 8.450 | 0.7483 | 6 | 8.250 | 0.5612 | 4 | 7.500 | 0.9823 | 4 | 7.600 | 0.8854 | 6 |

N = Number of measures used to calculate mean.
AD = Standard Deviation

TABLE 12

MPI Research Study Number 2382-001
J147: A 28-Day Oral (Gavage) Toxicity Study in Beagle Dogs with a 14-Day Recovery Period
Summary of Body Weight Values-FEMALE

| Endpoint | Study Interval (Day) | 0 mg/kg/day Mean | SD | N | 1 mg/kg/day Mean | SD | N | 10 mg/kg/day Mean | SD | N | 30 mg/kg/day Mean | SD | N |
|---|---|---|---|---|---|---|---|---|---|---|---|---|---|
| Body Weight kg | −1 | 6.333 | 0.3296 | 6 | 6.413 | 0.2955 | 4 | 6.325 | 0.3524 | 4 | 6.258 | 0.5074 | 6 |
| | 3 | 6.333 | 0.2927 | 6 | 6.463 | 0.3945 | 4 | 6.363 | 0.2898 | 4 | 6.308 | 0.5490 | 6 |
| | 7 | 6.333 | 0.3011 | 6 | 6.513 | 0.4070 | 4 | 6.250 | 0.3808 | 4 | 6.242 | 0.5238 | 6 |
| | 10 | 6.442 | 0.2853 | 6 | 6.675 | 0.4735 | 4 | 6.275 | 0.3686 | 4 | 6.192 | 0.6629 | 6 |
| | 14 | 6.475 | 0.2660 | 6 | 6.688 | 0.4090 | 4 | 6.150 | 0.3416 | 4 | 6.033 | 0.7508 | 6 |
| | 17 | 6.608 | 0.2635 | 6 | 6.763 | 0.3860 | 4 | 6.163 | 0.3425 | 4 | 5.858$^a$ | 0.6953 | 6 |
| | 21 | 6.558 | 0.2654 | 6 | 6.788 | 0.3945 | 4 | 6.063 | 0.4732 | 4 | 5.700$^b$ | 0.5320 | 6 |
| | 24 | 6.650 | 0.3406 | 6 | 6.813 | 0.4553 | 4 | 6.038 | 0.4308 | 4 | 5.575$^b$ | 0.4108 | 6 |
| | 28 | 6.675 | 0.3387 | 6 | 6.813 | 0.4347 | 4 | 5.988 | 0.3568 | 4 | 5.525$^b$ | 0.5194 | 6 |

N = Number of measures used to calculate mean.
AD = Standard Deviation
$^a$Significantly different from control, p < 0.05
$^b$Significantly different from control, p < 0.01

Example 4—Certain Non-Limiting Embodiments

A1. A method for treating or preventing obesity, assisting or inducing weight loss, suppressing apatite, or inhibiting weight gain in a subject comprising administering a therapeutically effective amount of a compound having a structure of Formula I:

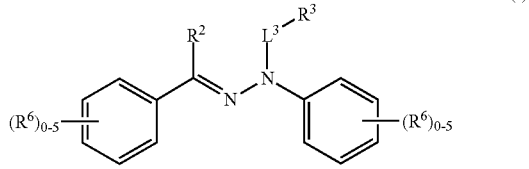

or a pharmaceutically acceptable salt, stereoisomer or tautomer thereof,
wherein:
$R^2$ is selected from the group consisting of H and methyl;
$R^3$ is trifluoromethyl or other fluoro substituted alkyl;
$L^3$ is a carbonyl; and
$R^6$ at each occurrence is independently selected from the group consisting of alkyl, methyl, methoxy, perfluoromethyl, perfluoromethoxy, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, substituted heterocyclic, halogen, cyano, cyanoalkyl, nitro, amino, amidino, carbamate, $S(O)_nR^7$ and $C(O)R^8$ or two $R^6$ at adjacent positions combine to form an optionally substituted heteroaryl or heteroalkyl ring fused with the adjoining phenyl moiety;
$R^7$ is H, $R^9$, $NH_2$, $HNR^9$ or $NR^9R^{10}$;
$R^8$ is OH, $OR^9$, $NH_2$, $NHR^9$ or $NR^9R^{10}$;
$R^9$ and $R^{10}$ at each occurrence are independently optionally substituted alkyl; and n=1 or 2.

A2. The method of embodiment A1, wherein $R^6$ at each occurrence is selected from the group consisting of alkyl, substituted alkyl, hydroxyl, alkoxy, substituted alkoxy, halogen, and $C(O)R^8$.

A3. The method of embodiment A2, wherein $R^6$ at each occurrence is selected from the group consisting of methyl, methoxy, perfluoromethyl, perfluoromethoxy, hydroxyl, Cl, F, and I.

A4. The method of embodiment A1, wherein the compound has the structure of Formula II;

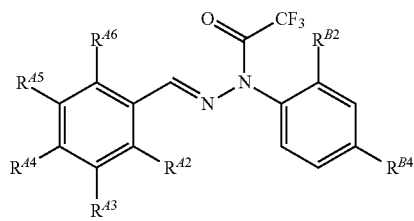

or a pharmaceutically acceptable salt, stereoisomer or tautomer thereof, wherein:
(i) $R^{42}$, $R^{44}$, $R^{45}$, and $R^{46}$ is H, $R^{43}$ is methoxy, $R^{B2}$ is methyl, and $R^{B4}$ is methyl; or
(ii) $R^{42}$, $R^{43}$, $R^{45}$, and $R^{46}$ is H, $R^{44}$ is methoxy, $R^{B2}$ is methyl, and $R^{B4}$ is methyl; or
(iii) $R^{42}$, $R^{43}$, $R^{44}$, $R^{45}$, and $R^{46}$ is H, $R^{B2}$ is H, and $R^{B4}$ is H; or
(iv) $R^{42}$, $R^{43}$, $R^{44}$, $R^{45}$, and $R^{46}$ is H, $R^{B2}$ is methyl, and $R^{B4}$ is methyl; or
(v) $R^{42}$, $R^{44}$, $R^{45}$, and $R^{46}$ is H, $R^{43}$ is methoxy, $R^{B2}$ is H, and $R^{B4}$ is H; or
(vi) $R^{42}$, $R^{43}$, $R^{44}$, $R^{45}$, and $R^{46}$ is H, $R^{B2}$ is H, and $R^{B4}$ is methyl; or
(vii) $R^{42}$, $R^{44}$, $R^{45}$, and $R^{46}$ is H, $R^{43}$ is methoxy, $R^{B2}$ is H, and $R^{B4}$ is methyl; or
(viii) $R^{42}$, $R^{43}$, $R^{44}$, $R^{45}$, and $R^{46}$ is H, $R^{B2}$ is methyl, and $R^{B4}$ is H; or
(ix) $R^{42}$, $R^{44}$, $R^{45}$, and $R^{46}$ is H, $R^{43}$ is methoxy, $R^{B2}$ is methyl, and $R^{B4}$ is H; or
(x) $R^{42}$, $R^{43}$, $R^{45}$, and $R^{46}$ is H, $R^{44}$ is COOH, $R^{B2}$ is methyl, and $R^{B4}$ is methyl; or
(xi) $R^{42}$, $R^{44}$, and $R^{45}$ is H, $R^{43}$ and $R^{46}$ is hydroxyl, $R^{B2}$ is methyl, and $R^{B4}$ is methyl; or
(xii) $R^{42}$, $R^{44}$, and $R^{46}$ is H, $R^{43}$ and $R^{45}$ is hydroxyl, $R^{B2}$ is methyl, and $R^{B4}$ is methyl; or
(xiii) $R^{42}$, $R^{44}$, and $R^{45}$ is H, $R^{43}$ is methoxy, $R^{46}$ is F, $R^{B2}$ is H, and $R^{B4}$ is Cl; or (xiv) $R^{A3}$ and $R^{A5}$ is H, $R^{A2}$ and $R^{A6}$ is F, $R^{A4}$ is hydroxyl, $R^{A6}$ is F, $R^{B2}$ is H, and $R^{B4}$ is F; or (xv) $R^{A2}$, $R^{A4}$, and $R^{A6}$ is H, $R^{A3}$ is hydroxyl, R is F, $R^{B2}$ is H, and $R^{B4}$ is F; or (xvi) $R^{A2}$, $R^{A5}$, and $R^{A6}$ is H, $R^{A3}$ and $R^{A4}$ taken together are —O—CH$_2$—O—, $R^{A5}$ is F, $R^{B2}$ is H, and $R^{B4}$ is F.

A5. The method of embodiment A4, wherein $R^{A2}$, $R^{A4}$, $R^{A5}$ and $R^{A6}$ is H, $R^{A3}$ is methoxy, $R^{B2}$ is methyl, and $R^{B4}$ is methyl.

B1. A method of preventing or treating obesity in a subject comprising administering to the subject a therapeutically effective amount of a compound of Formulas IV, or a pharmaceutically acceptable salt, stereoisomer or tautomer thereof.

C1. A method of preventing or treating obesity in a subject comprising administering to the subject a therapeutically effective amount of a compound selected from any one of Formulas I to IV, or a pharmaceutically acceptable salt, stereoisomer or tautomer thereof.

C1.1 A method of preventing weight gain in a subject comprising administering to the subject a therapeutically effective amount of a compound selected from any one of Formulas I to IV, or a pharmaceutically acceptable salt, stereoisomer or tautomer thereof.

C1.2 A method of inducing weight loss in a subject comprising administering to the subject a therapeutically effective amount of a compound selected from any one of Formulas I to IV, or a pharmaceutically acceptable salt, stereoisomer or tautomer thereof.

C1.3 A method of suppressing apatite in a subject comprising administering to the subject a therapeutically effective amount of a compound selected from any one of Formulas I to IV, or a pharmaceutically acceptable salt, stereoisomer or tautomer thereof.

C1.4. The method of any one of embodiments C1 to C1.3, wherein the subject is human.

C2. The method of any one of embodiments C1 to C1.4, wherein the compound comprises the structure of Formula I.

C3. The method of embodiment C2, wherein the compound comprises the structure of Formula III;

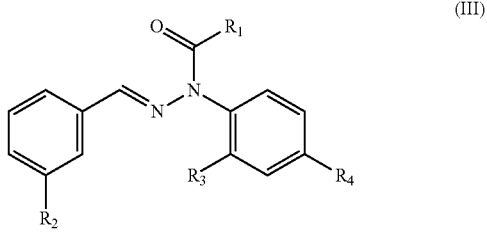

(III)

or a pharmaceutically acceptable salt, stereoisomer or tautomer thereof, wherein R$_1$ is methyl, fluoromethyl, difluoromethyl, trifluoromethyl, bromomethyl, dibromomethyl or tribromomethyl; R$_2$ is methyl, methoxy, hydroxyl, halogen, CF$_3$, OCH$_3$, OCF$_3$ or OCBr$_3$; and R$_3$ and R$_4$ are independently selected from hydrogen, hydroxyl, a halogen (e.g., Cl, F or Br), methyl, a methoxy, or an amine.

C4. The method of embodiment C3, wherein the compound comprises the structure of Formula IV;

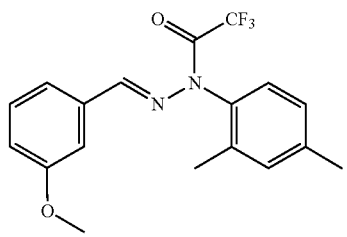

(IV)

or a pharmaceutically acceptable salt, stereoisomer or tautomer thereof.

C5. The method of any one of embodiments C1 to C4, wherein the compound is administered once a day, twice a day or three times a day.

C6. The method of any one of embodiments C1 to C5, wherein the compound is administered at a dose of 0.1 mg/kg to 100 mg/kg.

C7. The method of any one of embodiments C1 to C6, wherein the compound is administered orally or intravenously.

C8. The method of any one of embodiments C1 to C7, wherein the subject is obese.

C9. The method of any one of embodiments C1 to C8, wherein the subject has or has had a BMI of 30 or greater.

C10. The method of any one of embodiments C1 to C9, wherein the subject has a desire to loss body weight.

C11. The method of any one of embodiments C1 to C10, wherein the subject has an eating disorder.

C12. The method of any one of embodiments C1 to C11, wherein the subject has or is suspected of having bulimia.

C13. The method of any one of embodiments C1 to C12, wherein the subject has or is suspected of having a compulsive eating disorder or a binge eating disorder.

C14. The method of any one of embodiments C1 to C13, wherein the subject has a history of compulsive overeating or binge eating.

C15. The method of any one of embodiments C1 to C14, wherein the subject has a history of eating over 3000 calories/day.

C16. The method of any one of embodiments C1 to C15, wherein the subject is a human having a desire to lose weight.

C17. The method of any one of embodiments C1 to C16, wherein the subject has or is suspected of having diabetes.

C18. The method of any one of embodiments C1 to C17, wherein the subject has or is suspected of having cardiovascular disease.

C19. The method of any one of embodiments C1 to C18, wherein the subject is at risk of having or developing diabetes, heart disease or cardiovascular disease.

C20. The method of any one of embodiments C1 to C19, wherein the subject is a mammal.

C21. The method of C20, wherein the subject is a human.

C22. The method of C20, wherein the subject is a non-human primate.

C23. The method of C20, wherein the subject is a dog.

C24. The method of C20, wherein the subject is a cat.

D1. A compound comprising a structure selected from any one of Formula I, Formula II, Formula III and Formula IV for use in conducting a method of any one of embodiments C1 to C19.

D2. A pharmaceutical composition comprising a compound comprising a structure selected from any one of Formula I, Formula II, Formula III and Formula IV for use in conducting a method of any one of embodiments C1 to C19.

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein. Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

I claim:

1. A method of treating obesity, assisting or inducing weight loss, suppressing appetite, or inhibiting weight gain in a subject comprising administering to the subject a therapeutically effective amount of a compound selected from any one of Formula I,

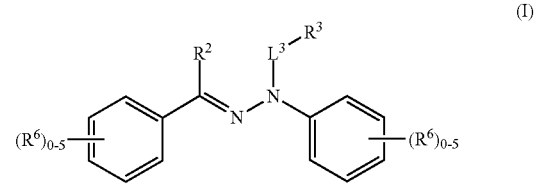

(I)

or a pharmaceutically acceptable salt, stereoisomer or tautomer thereof, wherein:

$R^2$ is selected from the group consisting of H and methyl;

$R^3$ is trifluoromethyl or other fluoro substituted alkyl;

$L^3$ is a carbonyl;

$R^6$ at each occurrence is independently selected from the group consisting of alkyl, substituted alkyl, cycloalkyl, substituted cycloalkyl, hydroxyl, alkoxy, substituted alkoxy, aryloxy, substituted aryloxy, mercapto, alkylthio, arylthio, carbonyl, aryl, substituted aryl, substituted heterocyclic, halogen, cyano, cyanoalkyl, nitro, amino, amidino, carbamate, $S(O)_nR^7$ and C(O)R$^8$ or two R$^6$ at adjacent positions combine to form an optionally substituted heteroaryl or heteroalkyl ring fused with the adjoining phenyl moiety;

R$^7$ is H, R$^9$, NH$_2$, HNR$^9$ or NR$^9$R$^{10}$;

R$^8$ is OH, OR$^9$, NH$_2$, NHR$^9$ or NR$^9$R$^{10}$;

R$^9$ and R$^{10}$ at each occurrence are independently optionally substituted alkyl; and n=1 or 2.

2. The method of claim 1, wherein the compound has the structure of Formula II;

(II)

[chemical structure]

or a pharmaceutically acceptable salt, stereoisomer or tautomer thereof, wherein:

(i) R$^{A2}$, R$^{A4}$, R$^{A5}$, and R$^{A6}$ is H, R$^{A3}$ is methoxy, R$^{B2}$ is methyl, and R$^{B4}$ is methyl; or (ii) R$^{A2}$, R$^{A3}$, R$^{A5}$, and R$^{A6}$ is H, R$^{A4}$ is methoxy, R$^{B2}$ is methyl, and R$^{B4}$ is methyl; or (iii) R$^{A2}$, R$^{A3}$, R$^{A4}$, R$^{A5}$, and R$^{A6}$ is H, R$^{B2}$ is H, and R$^{B4}$ is H; or (iv) R$^{A2}$, R$^{A3}$, R$^{A4}$, R$^{A5}$, and R$^{A6}$ is H, R$^{B2}$ is methyl, and R$^{B4}$ is methyl; or (v) R$^{A2}$, R$^{A4}$, R$^{A5}$, and R$^{A6}$ is H, R$^{A3}$ is methoxy, R$^{B2}$ is H, and R$^{B4}$ is H; or (vi) R$^{A2}$, R$^{A3}$, R$^{A4}$, R$^{A5}$, and R$^{A6}$ is H, R$^{B2}$ is H, and R$^{B4}$ is methyl; or (vii) R$^{A2}$, R$^{A4}$, R$^{A5}$, and R$^{A6}$ is H, R$^{A3}$ is methoxy, R$^{B2}$ is H, and R$^{B4}$ is methyl; or (viii) R$^{A2}$, R$^{A3}$, R$^{A4}$, R$^{A5}$, and R$^{A6}$ is H, R$^{B2}$ is methyl, and R$^{B4}$ is H; or (ix) R$^{A2}$, R$^{A4}$, R$^{A5}$, and R$^{A6}$ is H, R$^{A3}$ is methoxy, R$^{B2}$ is methyl, and R$^{B4}$ is H; or (x) R$^{A2}$, R$^{A3}$, R$^{A5}$, and R$^{A6}$ is H, R$^{A4}$ is COOH, R$^{B2}$ is methyl, and R$^{B4}$ is methyl; or (xi) R$^{A2}$, R$^{A4}$, and R$^{A5}$ is H, R$^{A3}$ and R$^{A6}$ is hydroxyl, R$^{B2}$ is methyl, and R$^{B4}$ is methyl; or (xii) R$^{A2}$, R$^{A4}$, and R$^{A6}$ is H, R$^{A3}$ and R$^{A5}$ is hydroxyl, R$^{B2}$ is methyl, and R$^{B4}$ is methyl; or (xiii) R$^{A2}$, R$^{A4}$, and R$^{A5}$ is H, R$^{A3}$ is methoxy, R$^{A6}$ is F, R$^{B2}$ is H, and R$^{B4}$ is Cl; or (xiv) R$^{A3}$ and R$^{A5}$ is H, R$^{A2}$ and R$^{A6}$ is F, R$^{A4}$ is hydroxyl, R$^{A6}$ is F, R$^{B2}$ is H, and R$^{B4}$ is F; or (xv) R$^{A2}$, R$^{A4}$, and R$^{A6}$ is H, R$^{A3}$ is hydroxyl, R$^{A5}$ is F, R$^{B2}$ is H, and R$^{B4}$ is F; or (xvi) R$^{A2}$, R$^{A5}$, and R$^{A6}$ is H, R$^{A3}$ and R$^{A4}$ taken together are —O—CH$_2$—O—, R$^{A5}$ is F, R$^{B2}$ is H, and R$^{B4}$ is F.

3. The method of claim 1, wherein the compound comprises the structure of Formula IV;

(IV)

[chemical structure]

or a pharmaceutically acceptable salt, stereoisomer or tautomer thereof.

4. The method of claim 1, wherein the subject is human.

5. The method of claim 1, wherein the compound is administered at a dose of 0.1 mg/kg to 1000 mg/kg.

6. The method of claim 5, wherein the compound is administered at a dose of 1 mg/kg to 300 mg/kg.

7. The method of claim 1, wherein the compound is administered orally or intravenously.

8. The method of claim 1, wherein the compound is formulated as a tablet or capsule.

9. The method of claim 8, wherein the tablet or capsule comprises 1, 5, 10, 50, 100 or 500 mg of the compound.

10. The method of claim 1, wherein the subject is an adult having a body mass index of 25 or more.

11. The method of claim 10, wherein the subject has a body mass index of 30 or more.

12. The method of claim 1, wherein the subject has or is at risk of having diabetes.

13. The method of claim 12, wherein the diabetes is type 2 diabetes.

14. The method of claim 1, wherein the subject has high blood pressure.

15. The method of claim 1, wherein the subject has fatty liver disease.

16. The method of claim 1, wherein the subject has, or is at risk of having heart disease or cardiovascular disease.

17. The method of claim 1, wherein the compound is administered once daily.

18. The method of claim 1, wherein the compound is administered 0.1 to 3 hours prior to exercise.

* * * * *